(12) United States Patent
Yasushi et al.

(10) Patent No.: US 7,245,960 B2
(45) Date of Patent: Jul. 17, 2007

(54) SYSTEM, METHOD, PROGRAM, AND MEDIUM FOR MEASURING HEART RATE

(75) Inventors: Mitsuo Yasushi, Tsurugashima (JP); Masatoshi Yanagidaira, Tsurugashima (JP)

(73) Assignee: Pioneer Corporation, Tokyo-to (JP)

( * ) Notice: Subject to any disclaimer, the term of this patent is extended or adjusted under 35 U.S.C. 154(b) by 221 days.

(21) Appl. No.: 10/649,858

(22) Filed: Aug. 28, 2003

(65) Prior Publication Data
US 2004/0044292 A1   Mar. 4, 2004

(30) Foreign Application Priority Data
Aug. 30, 2002   (JP) .......................... P2002-252447

(51) Int. Cl.
*A61B 5/04*   (2006.01)
(52) U.S. Cl. ...................... 600/509; 600/513
(58) Field of Classification Search ............... 600/509, 600/513
See application file for complete search history.

(56) References Cited

U.S. PATENT DOCUMENTS

| 4,680,708 A | * | 7/1987 | Ambos et al. ............. 600/509 |
| 4,732,158 A | * | 3/1988 | Sadeh ....................... 600/515 |
| 5,215,098 A | * | 6/1993 | Steinhaus et al. .......... 600/515 |
| 5,277,188 A | | 1/1994 | Selker ........................ 128/696 |
| 5,719,950 A | | 2/1998 | Osten et al. ................ 382/115 |

FOREIGN PATENT DOCUMENTS

| GB | 1496837 | 1/1978 |
| JP | 07-016214 | 1/1995 |
| JP | 07-508185 | 9/1995 |
| WO | WO 99/27463 | 6/1999 |

* cited by examiner

*Primary Examiner*—George R. Evanisko
*Assistant Examiner*—Alyssa M. Alter
(74) *Attorney, Agent, or Firm*—Drinker Biddle & Reath LLP

(57) ABSTRACT

A heart-rate measuring apparatus is provided a database, acquisition unit, production unit, search unit, cross-correlation processing unit, and calculation unit. In the database, one or more sets of electrocardiogram (ECG) waveform data, serving as reference waveform data, of persons being examined are stored in advance. The acquisition unit acquires a heartbeat signal from a person being examined. The production unit produces ECG waveform data based on the acquired heartbeat signal. On the basis of the produced ECG waveform data, the search unit searches the database for reference waveform data of the person. The cross-correlation processing unit performs cross-correlation processing between the produced ECG waveform data and the searched reference waveform data, and the calculation unit calculates the heart rate based on the cross-correlated ECG waveform data using values of R-R intervals of the waveform.

17 Claims, 13 Drawing Sheets

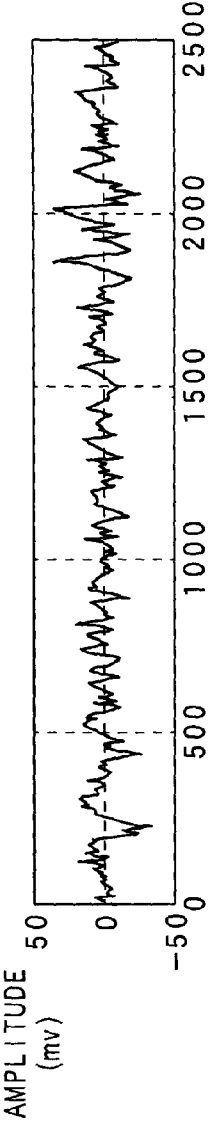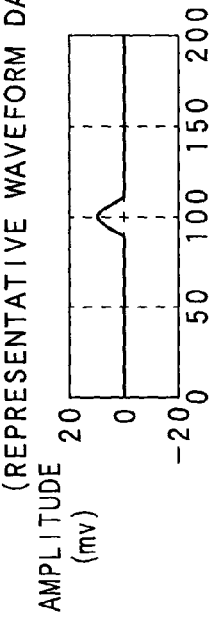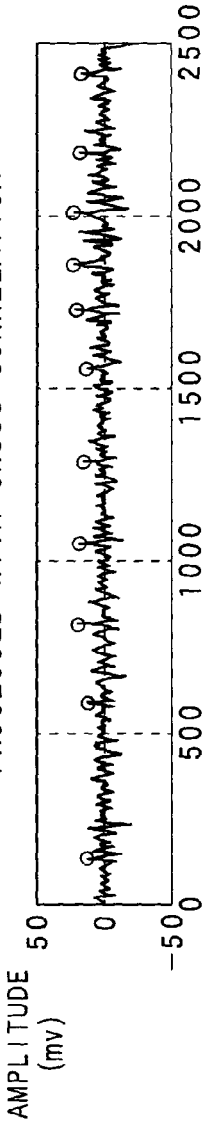

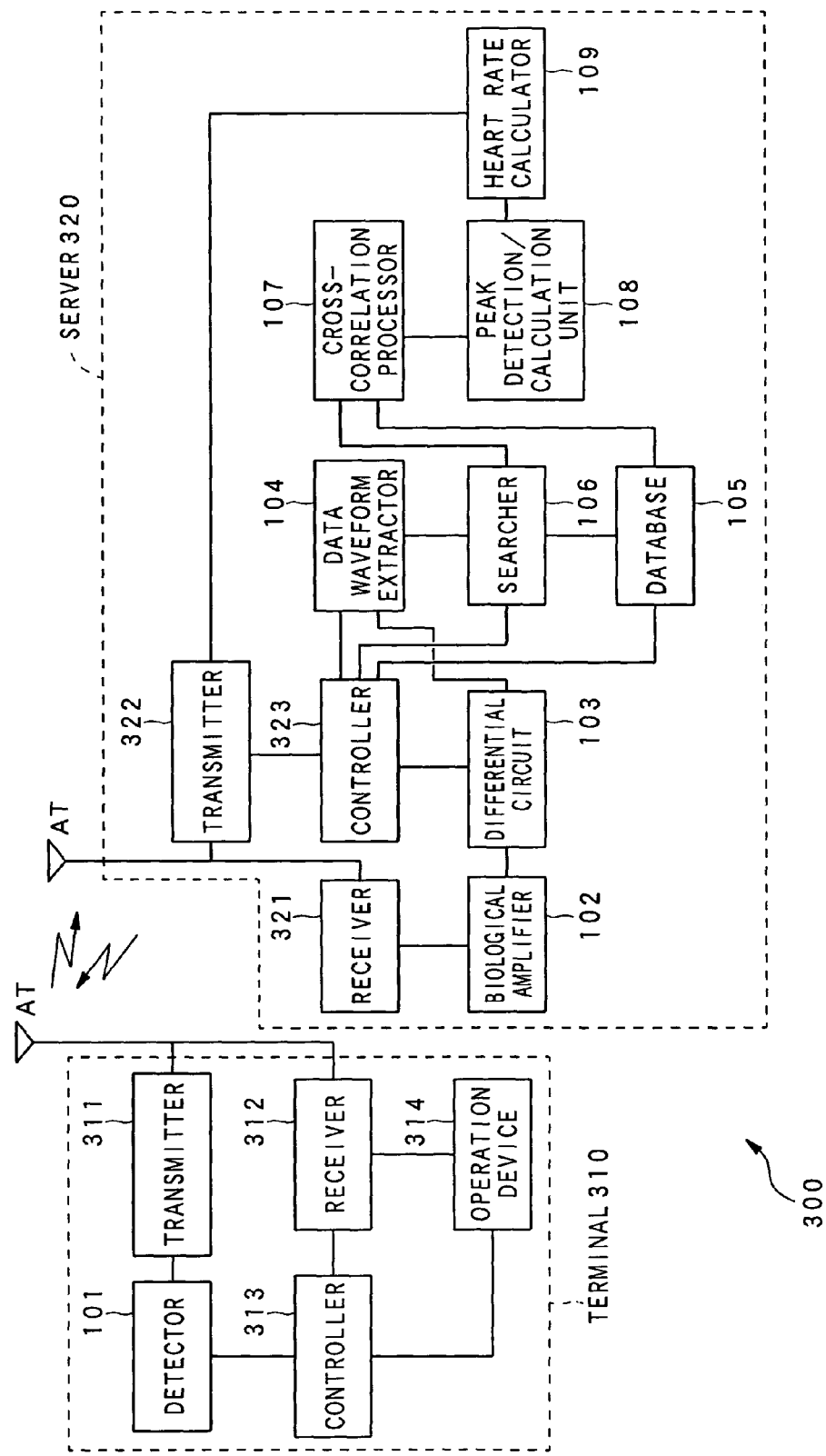

SYSTEM, METHOD, PROGRAM, AND MEDIUM FOR MEASURING HEART RATE

BACKGROUND OF THE INVENTION

1. Field of the Invention

The present invention relates to a method and system for measuring a heart rate of an object, such as a person to be examined, on the basis of a heartbeat signal acquired from the object.

2. Description of the Related Art

In recent years, applications of an electrocardiogram data indicative of the diastolic and systolic actions of the heart have been spread into various fields. Because it has been found that the influence of stress and fatigue caused in the human has come out as fluctuations in a heart rate or heart rate variability, the electrocardiogram data has been used in the field of human engineering and medical industry as well as the field of medical care, such as finding and diagnosis of cardiovascular diseases and monitoring medical conditions. Therefore, it is a recent demand to commercialize compact measurement apparatuses capable of measuring an amount of the heart rate and information in relation to heart rate variability.

As to the conventional measurement of the heart rate, there has been known an electrocardiogram analysis apparatus that is able to compute the heart rate based on a heart rate signal appearing due to excitation at the atrium of the heart. This type of electrocardiogram analysis apparatus is represented by the apparatus disclosed by Japanese Patent-laid Open (KOKAI) publication No. 1995-016214.

In this electrocardiogram analysis apparatus, a heartbeat signal is acquired from a person to be examined so that electrocardiogram (ECG) waveform data showing cyclically repeated movements of the heart can be obtained. This electrocardiogram waveform data is then subjected to detection of an R wave having a maximum peak and appearing every heartbeat in the electrocardiogram (ECG) waveform. Then peak-to-peak intervals (noted as R-R intervals) are detected, and used for calculating the heart rate of the person to be examined.

In detail, the operation for such a measurement carried out by the apparatus disclosed by the above publication is as follows.

First, the continuously acquired heartbeat signal is converted into electrocardiogram waveform data, and one frame of data in the electrocardiogram waveform data is sampled at a predetermined sampling frequency. The one frame of data is then subjected to pattern matching (cross-correlation processing) with previously prepared template data, which is a set of reference waveform data that imitates R waves, so that the R waves can be enhanced. Finally, an R-R interval, of which R waves have been enhanced, is obtained, subjected to computation of a reciprocal thereof, and multiplied by 60, whereby an amount of the heart rate per minute can be obtained.

However, the above conventional electrocardiogram analysis apparatus has suffered from the problem that error in the detection of R waves from the electrocardiogram waveform is obliged to be larger.

By nature, the measurement of the electrocardiogram waveform is affected largely by individual differences. Insufficient noise removal from the heart rate signal will spoil an accurate production of electrocardiogram waveform data.

In particular, the foregoing conventional electrocardiogram analysis apparatus has a poor performance in removing noise from the detected heart rate signal, because the pattern matching carried out in the conventional electrocardiogram analysis apparatus is not necessarily effective. Specifically, in the conventional electrocardiogram analysis apparatus, only wave elements collected from around an R wave (data from a range of 10 msec that covers an R wave), such as P wave and T wave, are pattern-matched with the reference waveform data. However, the electrocardiogram waveform elements, such as PQ interval, QT interval, and T-wave amplitude, have large influence resulting from individual differences, thus being apt to an erroneous detection of the R waves.

SUMMARY OF THE INVENTION

The present invention has been made in view of the above circumstances, and an object of the present invention is therefore to provide an apparatus, method, medium and computer-readable program, which are directed to, by way of example, heart rate detection with high precision.

The above object of the present invention can be achieved by a system for measuring a heart rate of the present invention. The system for measuring a heart rate, is provided with a database in which one or more sets of electrocardiogram waveform data of a living body are stored in advance, the electrocardiogram waveform data serving as reference waveform data; an acquisition unit for acquiring a heartbeat signal generated in the living body; a production unit for producing electrocardiogram waveform data of the living body based on the acquired heartbeat signal; a search unit for searching the database on the basis of produced waveform data served by the produced electrocardiogram waveform data, to specify the reference waveform data of the living body from which the heartbeat signal has been acquired; a cross-correlation processing unit for performing cross-correlation processing between the produced waveform data and the specified reference waveform data; and a calculation unit for calculating an extremal value every period of time from data subjected to the cross-correlation processing and calculating the heart rate based on the extremal value calculated every period of time.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In one aspect of the present invention can be achieved by the system for measuring a heart rate of the present invention. The system is, wherein the search unit is provided with a similarity calculating unit for calculating a similarity between the produced waveform data produced by the production unit and each set of the reference waveform data stored in the database; and a waveform data specifying unit for specifying, based on the calculated similarity, the reference waveform data of the living body from which the heartbeat signal has been acquired.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In another aspect of the present invention can be achieved by the system for measuring a heart rate of the present invention. The system is, wherein the similarity calculating unit is provided with a waveform cutting-out element for cutting out, every predetermined period of time, waveform data from the produced waveform data produced by the production unit; an average calculating element for calculating a single average waveform data based on the waveform data cut out every period of time; and a data similarity calculating element for calculating the similarity between the average waveform data and each set of the reference waveform data stored in the database, wherein the waveform data specifying unit is configured to specify, based on the calculated similarity, the reference waveform data of the living body from which the heartbeat signal has been acquired.

According to the present invention, this makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In further aspect of the present invention can be achieved by the system for measuring a heart rate of the present invention. The system is, wherein the waveform data specifying unit is configured to specify the average waveform data as being the reference waveform data, in cases where the similarity calculating unit determines that the similarity between the average waveform data and each set of the reference waveform data stored in the database is less than a predetermined value.

According to the present invention, this configuration makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In further aspect of the present invention can be achieved by the system for measuring a heart rate of the present invention. The system is, wherein the electrocardiogram waveform data produced as the produced waveform data by the production unit and each set of electrocardiogram waveform data stored as the reference waveform data in the database include identification information distinguishable from the other electrocardiogram waveform data, respectively; the system is further provided with a setting unit configured to set identification information to the produced waveform data produced by the production unit; the database configured to store therein the reference waveform data so as to relate to identification information inherent to the living body; and the search unit configured to search the database based on the indentation information of the produced waveform data, to specify the reference waveform data of the living body from which the heartbeat signal has been acquired.

According to the present invention, this configuration also makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In further aspect of the present invention can be achieved by the system for measuring a heart rate of the present invention. The system is, wherein the calculation unit is configured to calculate a local maximum between every predetermined area and to calculate the heart rate based on the local maximum.

According to the present invention, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

The above object of the present invention can be achieved by a method of measuring a heart rate of the present invention. The method is provided with a acquiring process of acquiring a heartbeat signal generated in a living body; a producing process of producing electrocardiogram waveform data of the living body based on the acquired heartbeat signal; a searching process of searching a database in which one or more sets of electrocardiogram waveform data of a living body are stored in advance, the electrocardiogram waveform data serving as reference waveform data, on the basis of produced waveform data served by the produced electrocardiogram waveform data, to specify the reference waveform data of the living body from which the heartbeat signal has been acquired; a performing process of performing cross-correlation processing between the produced waveform data and the specified reference waveform data; and a calculating process of calculating an extremal value every period of time from data subjected to the cross-correlation processing and the heart rate based on the extremal value calculated every period of time.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In one aspect of the present invention can be achieved by the method of measuring a heart rate of the present invention. The method is, wherein the search process is provided with a calculating process of calculating a similarity between the produced waveform data produced by the production unit and each set of the reference waveform data stored in the database; and a specifying process of specifying, based on the calculated similarity, the reference waveform data of the living body from which the heartbeat signal has been acquired.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In another aspect of the present invention can be achieved by the method of measuring a heart rate of the present invention. The method is, wherein the electrocardiogram waveform data produced as the produced waveform data by the production process and each set of electrocardiogram waveform data stored as the reference waveform data in the database include identification information distinguishable from the other electrocardiogram waveform data, respectively; the method is further provided with the setting process of setting identification information to the produced waveform data produced by the production process; and the searching process of searching the database in which the reference waveform data is stored so as to relate to identification information inherent to the living body, on the basis of the indentation information of the produced waveform data, to specify the reference waveform data of the living body from which the heartbeat signal has been acquired.

According to the present invention, this configuration also makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In further aspect of the present invention can be achieved by the method of measuring a heart rate of the present invention. The method is, wherein the identification information includes at least one of a name showing the living body and a characteristic amount in each set of electrocardiogram waveform information; the setting process sets, as the identification information, at least one of the name of the living body and the characteristic amount in the reference waveform data; and the searching process searches the database on the basis of the identification information of the produced waveform data, to specify the reference waveform data of the living body from which the heartbeat signal has been acquired, the database storing therein the reference waveform data made to relate to at least one of the name of the living body and the characteristic amount in the reference waveform data.

According to the present invention, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

The above object of the present invention can be achieved by a computer-readable program for measuring a heart rate of a living body of the present invention. The computer-readable program for measuring a heart rate of a living body based on a heartbeat signal acquired from the living body, the program making the computer function as: an acquiring device for acquiring a heartbeat signal generated in a living body; a producing device for producing electrocardiogram waveform data of the living body based on the acquired heartbeat signal; a searching device for searching a database in which one or more sets of electrocardiogram waveform data of a living body are stored in advance, the electrocardiogram waveform data serving as reference waveform data, on the basis of produced waveform data served by the produced electrocardiogram waveform data, to specify the reference waveform data of the living body from which the heartbeat signal has been acquired; a performing device for performing cross-correlation processing between the produced waveform data and the specified reference waveform data; and a calculating device for calculating an extremal value every period of time from data subjected to the cross-correlation processing and the heart rate based on the extremal value calculated every period of time.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In one aspect of the present invention can be achieved by the computer-readable program for measuring a heart rate of a living body of the present invention. The computer-readable program is, wherein when the computer is made to function as the searching device, the program makes the computer function as: a similarity calculating device for calculating a similarity between the produced waveform data produced by the producing device and each set of the reference waveform data stored in the database; and a waveform data specifying device for specifying, based on the calculated similarity, the reference waveform data of the living body from which the heartbeat signal has been acquired.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In another aspect of the present invention can be achieved by a computer-readable program for measuring a heart rate of a living body of the present invention. The computer-readable program is, wherein the electrocardiogram waveform data produced as the produced waveform data by the producing device and each set of electrocardiogram waveform data stored as the reference waveform data in the database include identification information distinguishable from the other electrocardiogram waveform data, respectively; wherein the program makes the computer function as a setting device for setting identification information to the produced waveform data produced by the producing device; and wherein the searching device searches the database in which the reference waveform data is stored so as to relate to identification information inherent to the living body, on the basis of the indentation information of the produced waveform data, to specify the reference waveform data of the living body from which the heartbeat signal has been acquired.

According to the present invention, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In further aspect of the present invention can be achieved by the computer-readable program for measuring a heart rate of a living body of the present invention. The computer-readable program is, wherein the identification information includes at least one of a name showing the living body and a characteristic amount in each set of electrocardiogram waveform information; wherein the program makes the computer function as: a setting device for setting, as the identification information, at least one of the name of the living body and the characteristic amount in the reference waveform data; and a searching device for searching the database on the basis of the identification information of the produced waveform data, to specify the reference waveform data of the living body from which the heartbeat signal has been acquired, the database storing therein the reference waveform data made to relate to at least one of the name of the living body and the characteristic amount in the reference waveform data.

The above object of the present invention can be achieved by an information record medium in which a computer-readable program for measuring a heart rate of a living body of the present invention. The information record medium in which a computer-readable program for measuring a heart rate of a living body based on a heartbeat signal acquired from the living body, the program making the computer function as: an acquiring device for acquiring a heartbeat signal generated in a living body; a producing device for producing electrocardiogram waveform data of the living body based on the acquired heartbeat signal; a searching device for searching a database in which one or more sets of electrocardiogram waveform data of a living body are stored in advance, the electrocardiogram waveform data serving as reference waveform data, on the basis of produced waveform data served by the produced electrocardiogram waveform data, to specify the reference waveform data of the living body from which the heartbeat signal has been acquired; a performing device for performing cross-correlation processing between the produced waveform data and the specified reference waveform data; and a calculating device for calculating an extremal value every period of time from data subjected to the cross-correlation processing and the heart rate based on the extremal value calculated every period of time.

According to the present invention, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

BRIEF DESCRIPTION OF THE DRAWINGS

Other objects and aspects of the present invention will become apparent from the following description and embodiments with reference to the accompanying drawings in which:

FIG. 5A shows one frame of electrocardiogram waveform data given to a conventional heart-rate measuring apparatus;

FIG. 5B shows a set of template data specified in the conventional heart-rate measuring apparatus;

FIG. 5C shows one frame of electrocardiogram waveform data subjected to cross-correlation processing in the conventional heart-rate measuring apparatus;

FIG. 13 is a block diagram showing the entire configuration of a heart rate measuring apparatus according to a fourth embodiment of the invention.

DETAILED DESCRIPTION OF THE PREFERRED EMBODIMENTS

Preferred embodiments of a heart-rate measuring apparatus according to the present invention will now be described with reference to the accompanying drawings.

First Embodiment

Figure 1:
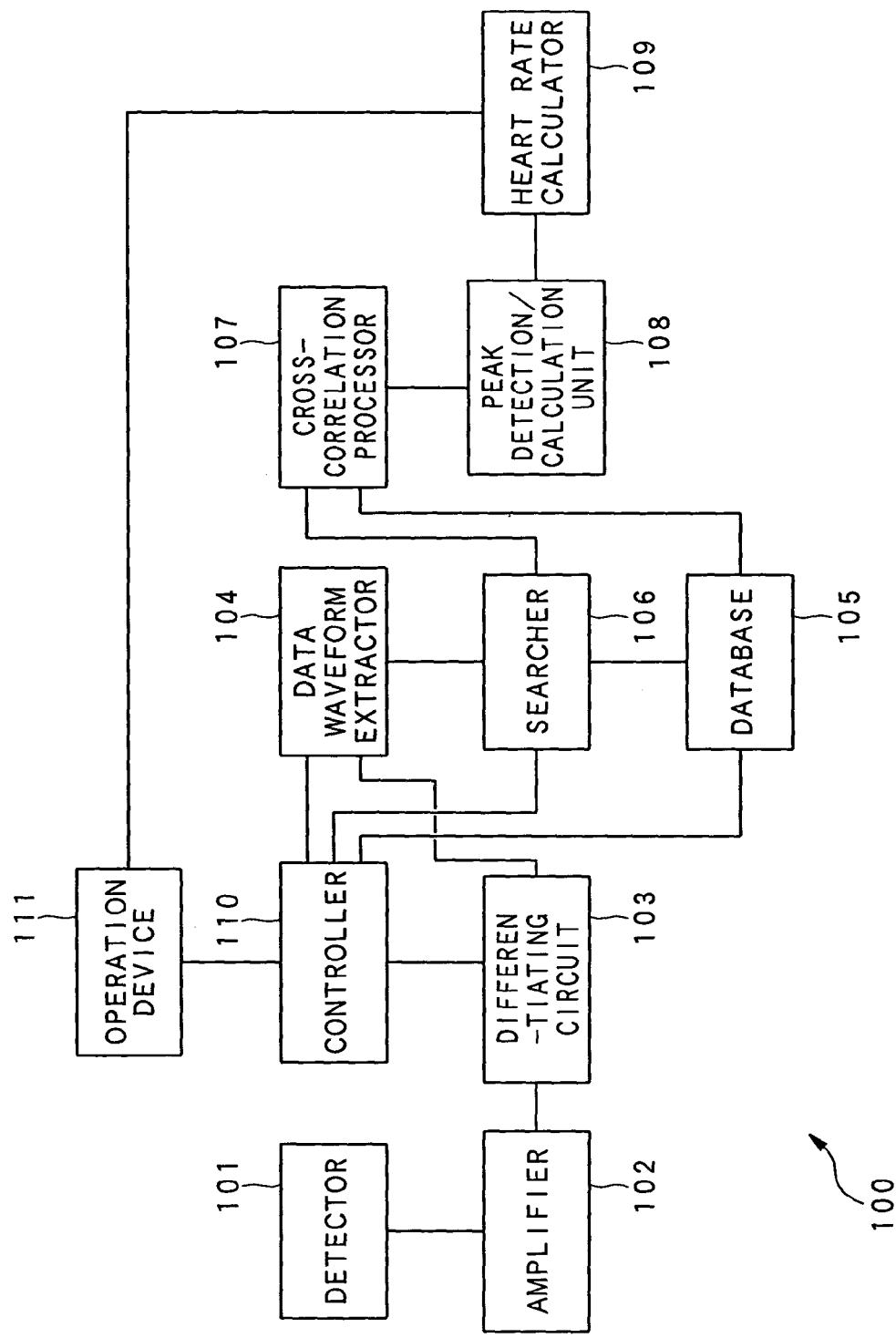
FIG. 1 is a block diagram showing the entire configuration of a heart rate measuring apparatus according to a first embodiment of the invention.

Referring to FIGS. 1 to 9, a first embodiment of the heart-rate measuring apparatus will now be described. First of all, FIG. 1 is used to explain the configuration of the heart-rate measuring apparatus according to this embodiment.

FIG. 1 shows the configuration of a heart-rate measuring apparatus 100 according to this embodiment.

In the present embodiment, as shown in FIG. 1, the heart-rate measuring apparatus 100 is provided with a detector 101 detecting a heartbeat signal from an object (human body); an amplifier 102 producing electrocardiogram waveform data based on the detected heartbeat signal; a differentiating circuit 103 removing lower-frequency components from the produced electrocardiogram waveform data; a data waveform extractor 104 extracting a single representative waveform data from the produced electrocardiogram waveform data; a database 105 in which a plurality of template data (described later) is stored in advance; a searcher 106 searching the database 105 for template data for an object to be examined or representative waveform data extracted based in electrocardiogram waveform data acquired from the object; a cross-correlation processor 107 performing cross-correlation processing between the produced electrocardiogram waveform data and the searched template data or the extracted template data; a peak detection/calculating unit 108 detecting, from the cross-correlated electrocardiogram waveform data, each R wave showing a peak value appearing every heartbeat, that is, appearing within each cardiac cycle, indicating periodically repeated movements and calculating an interval between two R waves (hereinafter referred to as an "R-R interval"); a heart rate calculator 109 calculating a heart rate using the calculated R-R intervals; a controller 110 controlling each component in this apparatus as well as determining whether or not the produced electrocardiogram waveform data has noise components; and an operation device 111 used for operating each necessary components arranged in this apparatus.

Of the above various components, by way of example, the detector 101 constitutes the acquisition unit according to the present invention, the biological amplifiers 102 constitutes a producing unit according to the present invention, the database 105 corresponds to the database according to the present invention, the searcher 106 functionally constitutes the searching unit, similarity calculating unit, and data waveform specifying unit according to the present invention.

Further, by way of example, the data waveform extractor 104 functionally constitutes the producing unit, similarity calculating unit, waveform cutting-out unit, average calculating unit, and data similarity calculating unit of the present invention, and the cross-correlation processor 107 forms the cross-correlation processing unit according to the present invention.

Still, by way of example, both of the peak detection/calculation unit 108 and the heart rate calculator 109 constitute cooperatively the calculating unit according to the present invention, and both of the operation device 111 and the controller 110 form the setting unit according to the present invention.

The detector 101 is configured, as an example, in such a manner that the detector 101 detects an electromotive force over a predetermined period of time from such a region as a human body's leg, arm, or chest region and provides the amplifier 102 with a heartbeat signal made up of the detected electromotive force.

The detector 101 is arranged, as an example, at part of the steering wheel of a not-shown automobile or any other vehicle, or at part of a health appliance. Thus, human's grasps of the detector 101 with both hands enables the detection of heartbeats indicative of a heartbeat signal indicative of changes in the action potential of the human heart, i.e., heartbeats indicative of the periodically repeated movements of the heart.

In the present embodiment, one frame is composed of 25,000 pieces of data acquired by sampling a heartbeat signal for 10 seconds at a sampling frequency of 250 Hz. Thus, the detector 101 is constructed to provide the amplifier 102 with the data thus detected.

To the amplifier 102 is provided the heartbeat signal detected by the detector 101, and the amplifier 102 is configured to amplify the inputted heartbeat signal to produce electrocardiogram waveform data from the heartbeat signal.

The electrocardiogram is a waveform representing temporal changes in the action potential in the human heart and composed of a serial of waves including the P wave, QRS wave, and T wave. One heartbeat, i.e., the waveform formed by one cardiac cycle of the electrocardiogram, is representatively shown as in FIG. 2.

The electrocardiogram waveform data, of which one cardiac cycle is in FIG. 2, will now be described.

Figure 2:
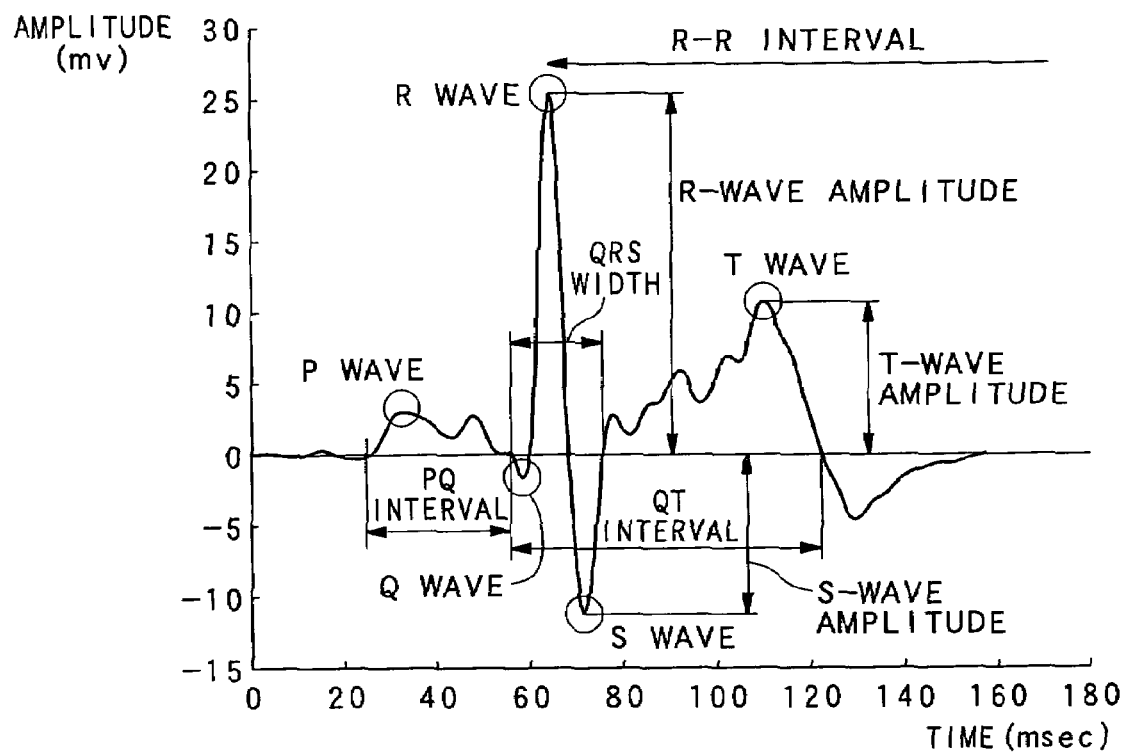
FIG. 2 illustrates essential waves of an electrocardiogram waveform to be repeated cyclically.

FIG. 2 is a graph representatively showing one cardiac cycle of the electrocardiogram waveform data.

The P wave shown in FIG. 2 is caused by excitation of the atrium muscle and appears when the atrium contacts in response to the fact that an electric stimulation generated at the auricular node has been sent to the entire atrium. The auricular node, which can be said as a control tower, plays as an electric switch located in the right atrium of the heart.

The Q wave, R wave, and S wave, all of which represent the excitation of the ventricular muscle, appear responsively to the contraction of the entire ventricles caused by the electric stimulation from the atrium. Of these waves, the Q wave provides a maximum amplitude within each cardiac cycle.

The T wave shows a process during which the excitation of the ventricular muscle is subjected to recovery regression and appears while the current flowing in the ventricles fades away in time.

The heart moves periodically, thus providing the electrocardiogram repeated every heartbeat, as shown in FIG. 2 representing only one cardiac cycle of the electrocardiogram. In this electrocardiogram, there is a period of about 100 msec covering the appearances of the P, Q and S waves, with the R wave located at the middle of the period. Hence, the acquisition of the heartbeat signal for about 10 seconds allows the amplifier 102 to acquire about 10 sets of waveform data representing each cardiac cycle in the electrocardiogram waveform data.

Hence the amplifier 102 produces electrocardiogram waveform data, which can be shown as in FIG. 2, from an electromotive force generated within the human body and detected therefrom, and provides the produced data to the differentiating circuit 103.

The differentiating circuit 103, which will receive the electrocardiogram waveform data produced by the amplifier 102, applies differentiating operation to the received electrocardiogram waveform data to remove its lower-frequency components. Hence, resultant electrocardiogram waveform data, from which the lower-frequency components have been removed, is sent to the data waveform extractor 104.

The data waveform extractor 104 receives the electrocardiogram waveform data from the differentiating circuit 103, and produces a signal representative waveform data from the one frame of received electrocardiogram waveform data (hereinafter, this processing is referred to as "representative waveform data production processing"). This extractor 104 is configured to provide the searcher 106 or the database 105 with the resultant representative waveform data.

To be specific (refer to FIGS. 3A to 3C), the data waveform extractor 104 applies detection processing to the received electrocardiogram waveform data showing periodic fluctuations, so that an R wave representing a maximum amplitude is detected in each period of time considered one cardiac cycle. This detection is carried out every period over a plurality of periods determined in advance. The data waveform extractor 104 then calculates an "R-R interval" indicative of an interval of time between mutually adjacent two R waves that have been detected and this calculation is repeated every R wave. Then the data waveform extractor 104 uses data of each R-R interval to superpose the waveform data (t1, t2, . . . , t10) one on another so that the data are weight-averaged to make one-heartbeat (one-cardiac-cycle) waveform data. Finally, the data waveform extractor 104 applies a window function, such as a Hanning window, to the superposed waveform data in order to produce a representative waveform data. Therefore, these processes enable the data waveform extractor 104 to produce the representative waveform data.

Figure 3A:
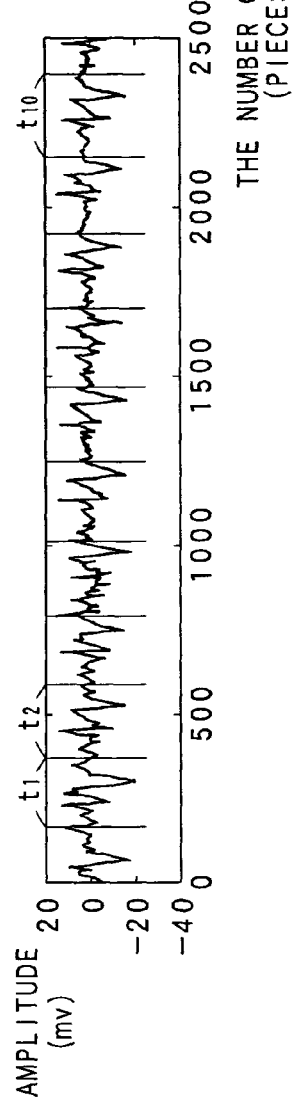
FIG. 3A shows one frame of electrocardiogram waveform data given to a data waveform extractor in the first embodiment.
Figure 3C:
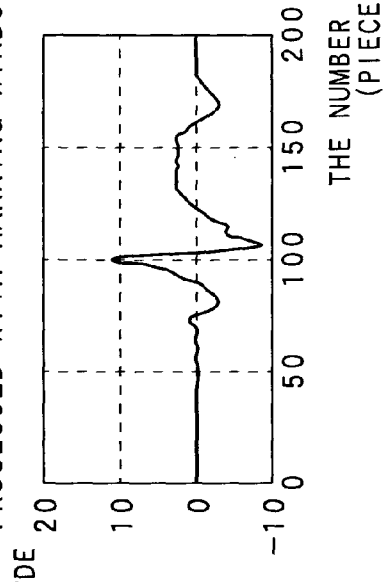
FIG. 3C shows electrocardiogram waveform data produced by applying the Hanning window function to the waveform data shown in FIG. 3B.
Figure 3B:
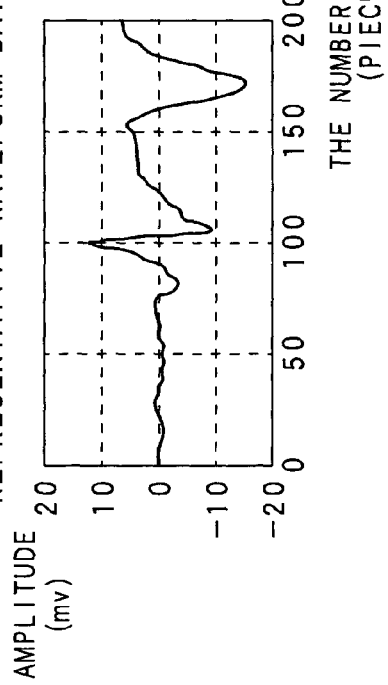
FIG. 3B shows a set of specified-length electrocardiogram waveform data formed by cutting out specified-length data, every cardiac cycle, from the one frame of electrocardiogram waveform data given to the data waveform extractor and mutually superposing a plurality of sets of cut-out data.

FIG. 3A exemplifies one frame of electrocardiogram waveform data that has been sent to the data waveform extractor 104, FIG. 3B exemplifies one set of electrocardiogram waveform data formed by cutting out each set of specified-length data, every cardiac cycle, from the one frame of electrocardiogram waveform data and superposing the plural cut-out data one on another, and FIG. 3C exemplifies electrocardiogram waveform data produced by applying the Hanning window function to the waveform data shown in FIG. 3B.

By way of example, the thus-produced repetitive waveform data constitutes the average waveform data according to the present invention.

Figure 4:
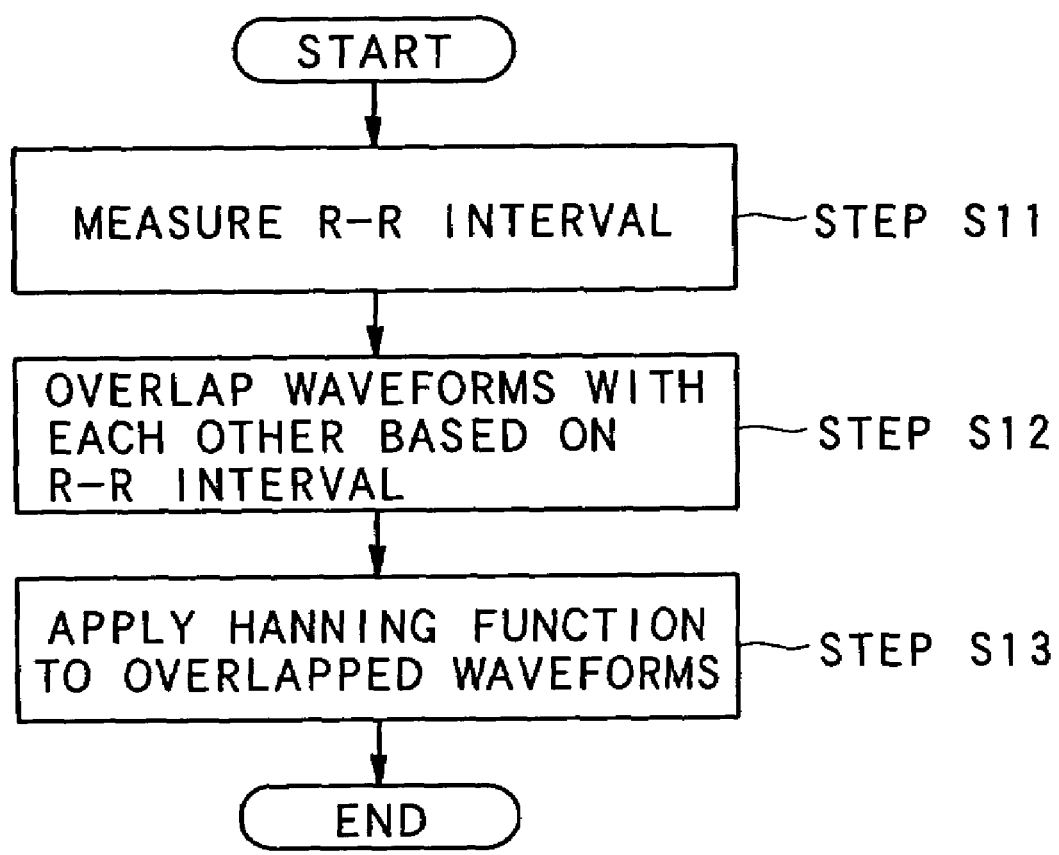
FIG. 4 is a flowchart showing the processing for producing a representative waveform data, which is carried out by the data waveform extractor in the first embodiment.

Referring to FIG. 4, the representative waveform data production processing, which is carried out by the data waveform extractor 104, will now be described.

FIG. 4 is a flowchart showing the operation of the representative waveform data production processing, which is carried out by the data waveform extractor 104.

First, the data waveform extractor 104 detects, from the electrocardiogram waveform data, a maximum of data within a period of time (tn) considered to be a period of one heartbeat determined previously, that is, an R wave appearing within each cardiac cycle, and then calculates each R-R interval (step S11).

The data waveform extractor 104 then superposes the data over each cardiac cycle one on another on the basis of the calculated R-R intervals, which will produce the waveform data that has been weight-averaged over one heartbeat, i.e., over one cardiac cycle (step S12).

The data waveform extractor 104 finally applies a window function, which is for example a Hanning function, to the superposed waveform data, whereby a representative waveform data is produced (step S13).

Accordingly, the data waveform extractor 104 is able to produce a representative waveform data through the foregoing steps.

Although the representative waveform data production processing in the present embodiment has used the Hanning function as the window function, this is not a definitive list. Other window functions may also be applicable to the representative waveform data production processing.

The database 105 is used to previously store template data therein, the template data being one or more sets of reference waveform data. This database 105 is subjected to a search based on the name of a person to be examined and a representative waveform data when template data is set and processed in the database 105. In cases where targeted template data is present (i.e., one set of specific template data is found) in the database 105, the template data is outputted to the cross-correlation processor 107.

Concretely, the database 105 has memorized template data consisting of electrocardiogram waveform data assigned to a period of 100 msec including the P, Q and S waves with the R wave located at the middle of the period, as shown in FIG. 3, with the template data related to each person to be examined.

Further, as will be described later, the database 105 operates responsively to commands from the controller 110 to receive a set of representative waveform data newly extracted from the data waveform extractor 104 and memorizes the received data as template data.

In addition, the names of persons to be examined and representative waveform data are allowed to be inputted to the searcher 106. Thus, based on an inputted person's name or inputted representative waveform data, the searcher 106 is entitled to search the database 105 for template data of a person to be examined who has been specified by the inputted person's name or by the inputted representative waveform data.

To be specific, for setting template data based on a person's name, the searcher 106 searches the database 105 for template data of which person's name agrees with the inputted person's name. If there is a set of template data corresponding to the specified person's name in the database 105, the database 105 is controlled so that the specified template data is provided to the cross-correlation processor 107.

Further, for setting template data based on representative waveform data, the searcher 106 calculates a similarity between the inputted representative waveform data and each of the sets of template waveform data stored in the database 105. Then, if finding a set of template data closely related in the similarity to the inputted electrocardiogram waveform data, the searcher 106 causes the database 105 to send out the closely related template data to the cross-correlation processor 107.

In the present embodiment, the searcher 106 is configured to compute a correlation value between a set of representative waveform data and each set of template data as a parameter to measure the similarity therebetween, and uses the computed correlation value to search the database 105.

For instance, the searcher 106 calculates the absolute value $\epsilon_n$ of a difference between the set of representative waveform data and each set of template data based on the formula (1):

$$\epsilon_0 < \epsilon_n = |y_0 - y_n| (n=1, 2, \ldots, k) \tag{1},$$

in which $y_0$ denotes the inputted representative waveform data; y1, y2, ..., yn denotes the template data stored in the database 105.

The searcher 106 then determines whether or not each absolute value $\epsilon_n$ is larger than a predetermined threshold $\epsilon_0$. When this determination reveals that the database 105 has template data showing each absolute value $\epsilon_n$ larger than the threshold $\epsilon_0$, such template data is provided as new representative waveform data to the cross-correlation processor 107.

It is preferred that the absolute value $\epsilon_0$, which is a threshold, is generally 0.6 or more. Hence, in the present embodiment, in cases where the calculation shows that pluralities of sets of template data have absolute values $\epsilon$ equal or higher to or than 0.6, the template data that shows an absolute value, among the absolute values $\epsilon$, which is the closest to 1.0 is selected and supplied to the cross-correlation processor 107.

In contrast, if the foregoing determination shows that the inputted representative waveform data is related at low cross correlation values to any set of template data stored in the database 105; in other words, each absolute value $\epsilon_n$ to each set of template data is lower than the predetermined threshold $\epsilon_0$, a notification that there is no necessary template data is made toward the controller 110. In this case (i.e., necessary template data is unavailable), the representative waveform data that has been subjected to computing the absolute values is supplied to the cross correlation processor 107 as the template data.

In the present embodiment, the controller 110 is configured to use the operation device 111 to urge an operator to enter a person's name corresponding to the representative waveform data that has been subjected to computing the absolute values. And, if the person's name is inputted, the controller 111 allows the database 105 to accept the representative waveform data (template data) made to relate to the person's name.

The cross-correlation processor 107 receives both of the electrocardiogram waveform data from which lower-frequency components have already been removed and either of the template data (waveform data) provided from the database 105 or the representative waveform data produced as template data by the data waveform extractor 104. The cross-correlation processor 107 thus applies cross-correlation processing to both the provided electrocardiogram waveform data and the provided template data, before the processor 107 supplies the peak detection/calculation unit 108 with the electrocardiogram waveform data that has experienced the cross correlation processing.

More concretely, the cross-correlation processor 107 is configured to give, every predetermined period of time, a delay time to the template data so as to be delayed from the electrocardiogram waveform data. The processor 107 then calculates a cross-correlation function as to each of the delay times, and provides the peak detection/calculation unit 108 with a value of the cross-correlation function, which is obtained every delay time.

For instance, the cross-correlation processor 107 according to the present embodiment calculates $R_{xy}$ defined by the equation (2):

$$R_{xy}(t) = \lim_{T \to 0} \frac{1}{T} \int_{-\frac{T}{2}}^{\frac{T}{2}} x(t) y(t + \tau) \, dt, \tag{2}$$

where x denotes the electrocardiogram waveform data of which lower-frequency components have been removed, y denotes the template data, $\tau$ denotes a delay time. Based on the formula (2), the processor 107 calculates the value $R_{xy}$ every time the delay time $\tau$ is shifted by a predetermined amount, and provides a value of the cross-correlation function to the peak detection/calculation unit 108.

Figure 6A:
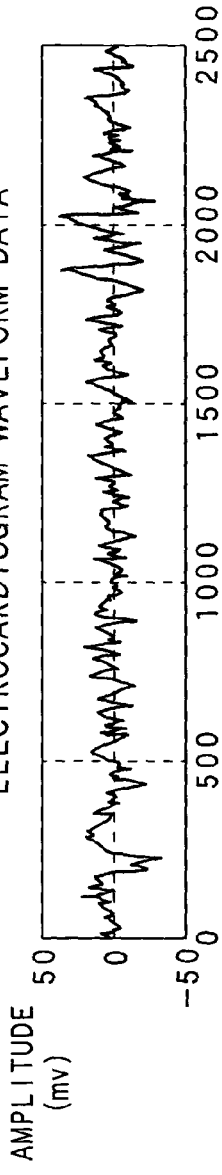
FIG. 6A shows one frame of electrocardiogram waveform data given to the data waveform extractor in the first embodiment.
Figure 6B:
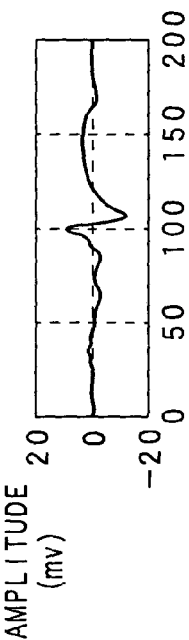
FIG. 6B shows a set of template data specified in the first embodiment.
Figure 6C:
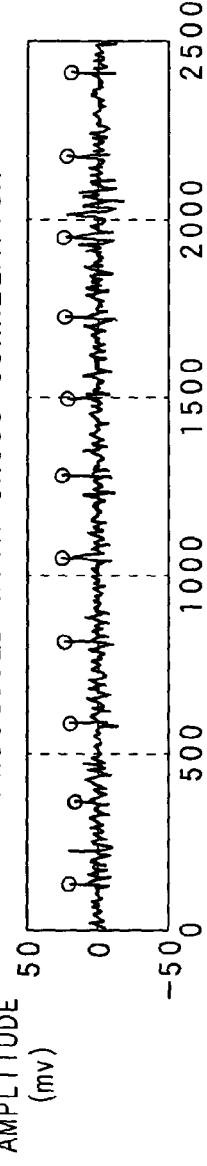
FIG. 6C shows one frame of electrocardiogram waveform data subjected to cross-correlation processing in the first embodiment.

Electrocardiogram waveform data calculated based on the conventional heart-rate measuring technique, which is shown in FIGS. 5A to 5C, and electrocardiogram waveform data created by the cross-correlation processing carried out by the cross-correlation processor 107, which is shown in FIGS. 6A to 6C, will now be described in a comparative manner.

As shown in FIG. 5C, the conventional heart-rate measuring technique adopts pattern matching applied to reference waveform data based on attribute data obtained around the R wave. As a result, personal differences in the electrocardiogram waveform, which are attribute data including a PQ interval, QT interval, and T-wave amplitude, deteriorate a noise removal capability necessary for detected electrocardiogram waveform data. Practically, as FIG. 5C illustrates in its graph, waves marked by circles do not appear at certain intervals, thus making it difficult to find a waveform peak that should exist during each certain period of time, i.e., every one cardiac cycle (every one heartbeat), thus leading to erroneous detection.

In contrast, as illustrated in FIG. 6C, the heart-rate measuring technique used in the present embodiment is directed to use of electrocardiogram waveform data of which data acquisition time range is 100 msec covering the P, Q and S waves, with the R-wave located at the middle of the range. Hence, it is possible to remove noise, without fail, from the detected electrocardiogram waveform data. This effect is shown in FIG. 6C, in which waves marked by circles appear at certain intervals, thus making it possible to detect the peaks surely.

Incidentally, FIG. 5A exemplifies one frame of electrocardiogram waveform data inputted to the conventional heart-rate measuring apparatus, FIG. 5B exemplifies template data specified in the searcher 106, and FIG. 5C exemplifies the electrocardiogram waveform data obtained after the cross-correlation processing. Meanwhile, FIG. 6A exemplifies one frame of electrocardiogram waveform data inputted to the heart-rate measuring apparatus according to the present embodiment, FIG. 6B exemplifies template data specified in the searcher 106, and FIG. 6C exemplifies the electrocardiogram waveform data obtained after the cross-correlation processing.

The peak detection/calculation unit 108 receives the data calculated by the cross-correlation processing (hereinafter referred to as "cross-correlation processed data"). Practically, the values $R_{xy}$ resulting from the calculation on the equation (2) are provided to the unit 108.

The peak detection/calculation unit 108 is configured to detect waveform peaks from the received cross-correlation process data, and then, using data indicative of a peak waveform has been detected (hereinafter referred to as "peak waveform data"), to calculate an interval of time from a certain peak to the next peak (peak to peak interval), that is, R-R interval. The peak detection/calculation unit 108 is configured to provide the heart rate calculator 109 with values showing peak to peak intervals, on the basis of the calculated R-R intervals.

For instance, the peak detection/calculation unit 108 computes an average of the R-R intervals and treats it as the value indicating the peak to peak intervals (hereinafter referred to as "peak-to-peak interval"). The unit 108 outputs the peak-to-peak value to the heart rate calculator 109.

The heart rate calculator 109, which will receive the peak-to-peak value from the peak detection/calculation unit 108, is configured to figure out a reciprocal of the received peak-to-peak value, multiply the resultant reciprocal by 60 to obtain a heart rate per minute, and sends out the calculated heart rate to an external unit.

In the present embodiment, the external output of the heart rate calculated by the heart rate calculator 109 is only an example. Instead of this external output or in parallel with this external output, the heart rate resulting from the calculation can be provided on a display mounted to the operation device 111.

The controller 110 operates to control each component of this apparatus in response to commands issued from the operation device 111 or electrocardiogram waveform data outputted from the differentiating circuit 103.

Concerning the electrocardiogram waveform data from the differentiating circuit 103, the controller 110 always monitors this data about whether or not there is less noise superimposed on the electrocardiogram waveform data from the differentiating circuit 103. The controller 103 controls each component so that template data is generated based on such electrocardiogram waveform data, provided that it is determined that there is less noise on the electrocardiogram waveform data.

Specifically, the controller 110 calculates a standard deviation (σ) of the R-R intervals in the differentiated electrocardiogram waveform data, and draws a comparison between the standard deviation (σ) and a predetermined threshold. If the calculated standard deviation (σ) is less than the threshold, the controller 110 concludes that there is no noise, thus operating to give the output of the differentiating circuit 103 to the data waveform extractor 104. Further, the controller 110 controls the data waveform extractor 104 so that template data is produced from the differentiated electrocardiogram waveform data.

Still further, in cases where the searcher 106 could not find necessary waveform data among the template data stored in the database 105, the controller acts in the same manner as the above. Namely, even in such a case, the controller 110 controls the data waveform extractor 104 to make it produce the template data. In addition, in this case, it is determined whether or not the differentiated electrocardiogram waveform data includes less noise components. If this determination shows that the electrocardiogram waveform data includes noise components of which amount is above a pre-given amount, the controller 110 issues an alarm that instructs an operator or an object to be examined to re-detect the heartbeat signal.

Moreover, when the name of a person subjected to the heart rate measurement is given in advance via the operation device 111, the controller 110 is programmed to control the searcher 106 to search database 105 for template data of the person. Based on the searched template data, the controller 110 orders the performance of both the cross-correlation processing and the heart rate calculation.

The operation device 111 is provided with, for instance, a plurality of switches and a display portion (both not shown). While viewing a screen on the display portion, an operator is able to use the switches to select and specify a person to be examined.

Figure 7:
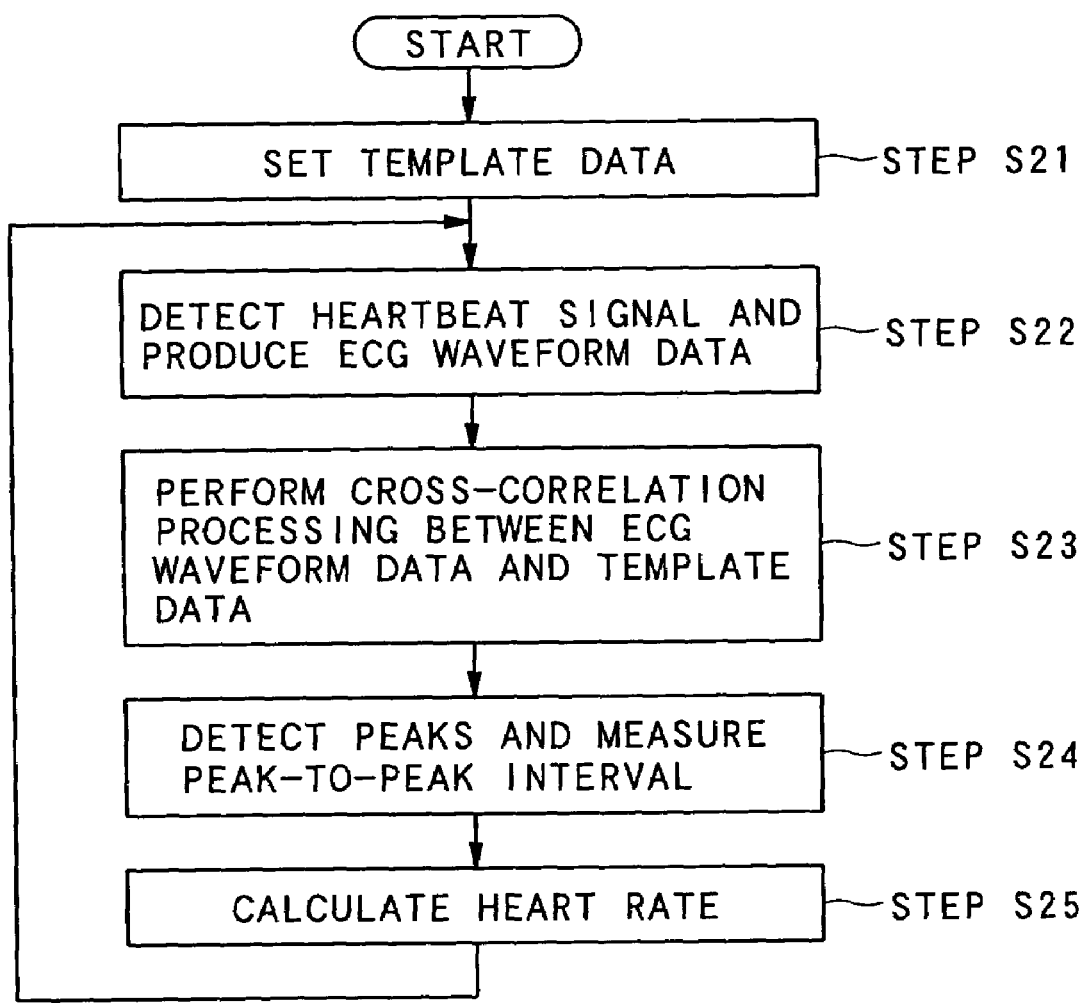
FIG. 7 is a flowchart explaining the heart-rate measurement operation carried out in the first embodiment.

Referring to FIG. 7, the operation necessary for the heart rate measurement will now be explained.

FIG. 7 shows a flowchart for the heart rate measurement carried out cooperatively by predetermined components each operating under the control of the controller 110.

In the present embodiment, the detector 101 is attached to a steering wheel.

First, the operation device 111 is operated by a person (for example, a driver) to be examined, so that a command to start the heart rate measurement is given to the controller 110. In response to this command, the controller 110 performs processing for setting template data (hereinafter referred to as "template setting processing") by controlling the data waveform extractor 104, searcher 106 and database 105 based on individual authentication involving some operations carried out by the person to be examined (step S21).

This setting processing for template data, which is carried out by the controller 110, will be detailed later.

The controller 110 then prompts the person to grasp the steering wheel. When the person moves to grasp the steering wheel, the controller 110 detects such a grasp, and then allows the detector 101 to detect a heartbeat signal and the amplifier 102 to produce electrocardiogram waveform data. Also the controller 110 performs the control such that the electrocardiogram waveform data is sent to the differentiating circuit 103 to remove lower-frequency components from the electrocardiogram waveform data. Thus, the resultant electrocardiogram waveform data with its lower-frequency components is sent to the cross-correlation processor 107 (step S22).

As a modification, the controller 110 may operates as follows. That is, in cases where the template setting processing (step S21) is conducted before the processing at step S22, the controller 110 may act such that, with no electrocardiogram waveform data produced at step S22, the template setting processing produces electrocardiogram waveform data to be sent to the cross-correlation processor 7.

The controller 110 then controls the cross-correlation processor 107 such that cross-correlation processing is performed using both of the template data set by the template setting possessing described later and the electrocardiogram waveform data obtained via the differentiating circuit 103 (step S23).

Then, the controller 110 proceeds to the next step, where the cross-correlated electrocardiogram waveform data is sent to the peak detection/calculation unit 108. By this unit 108, an R wave is detected every cardiac cycle, i.e., every one heartbeat, and a peak-to-peak interval from each peak to the next peak is calculated, thus a peak-to-peak interval value being provided (step S24).

At last, the controller 110 controls the heart rate calculator 109 so that it calculates a reciprocal of the peak-to-peak interval, multiplies the reciprocal by 60 to figure out a heart rate, and outputs the calculated heart rate to the operation device 111 or to an externally placed unit (step S25).

Once the foregoing processing is started, it is usual that the processes at steps S22 to S25 are repeated at specific intervals. As a result, a heart rate is calculated consecutively at specific intervals and outputted to the operation device 111 or an external unit.

Figure 8:
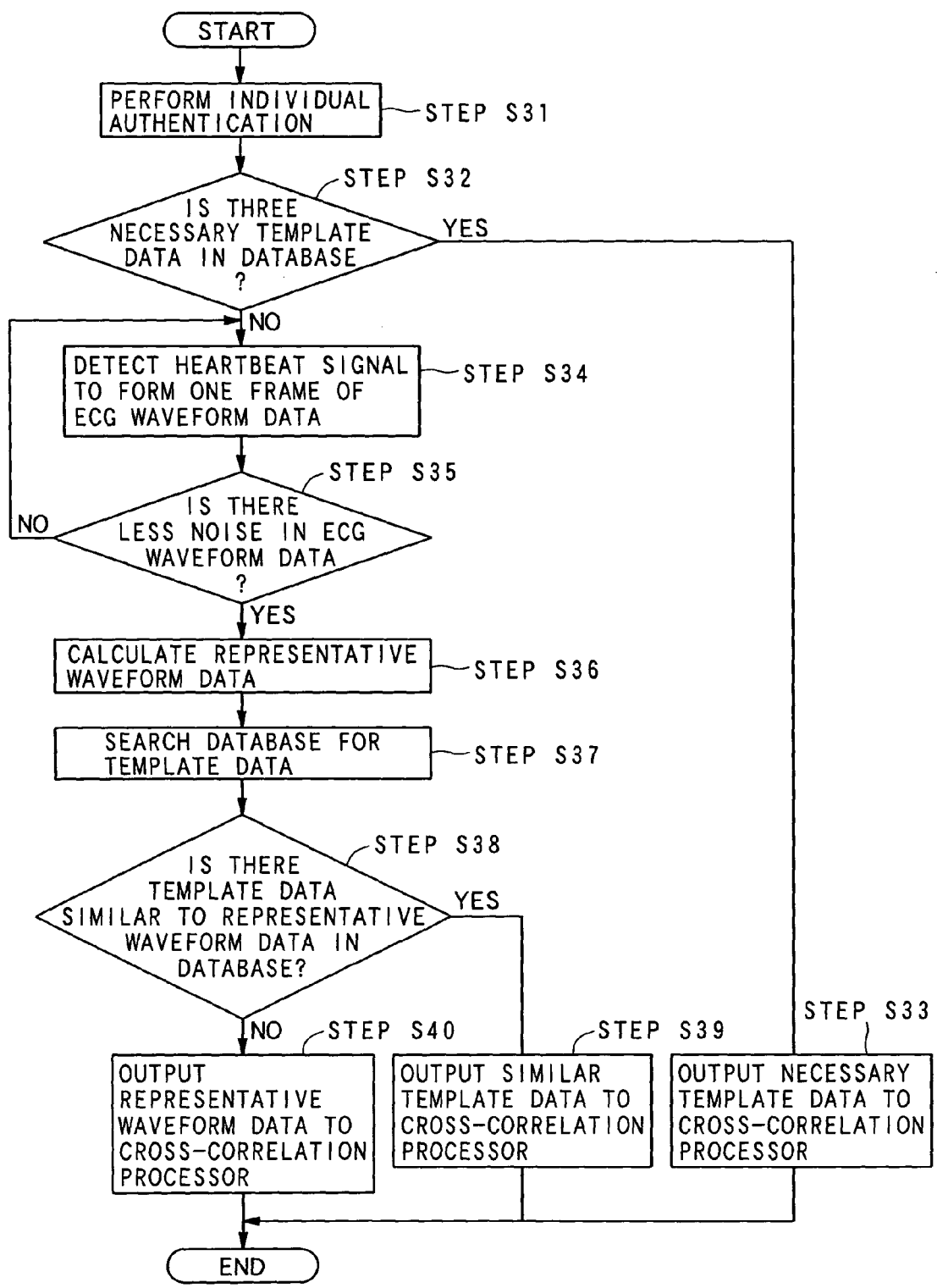
FIG. 8 is a flowchart explaining the processing for setting template data in the first embodiment.

Referring to FIG. 8, the processing for setting template data, which is carried out by the data waveform extractor 104, will now be described.

FIG. 8 is a flowchart explaining the processing operation to set template data, which is executed cooperatively by predetermined components placed under the control of the controller 110.

First, the operation device 111 is operated by a person to be examined, so that a command to start the heart rate measurement is given to the controller 110. In response to this command, the controller 110 uses not-shown plural switches and display portion placed on the operation device 111 so as to command the person to take necessary steps for individual authentication. That is, the controller 110 prompts the person to enter a person's name. When receiving information indicative of the person's name, the controller 110 proceeds to the individual authentication (step S31).

In the present embodiment, the individual authentication is performed, by way of example, by using the display portion on the operation device 111. Namely, a list of the names of persons to be examined, which has been registered beforehand, is visualized on the display portion. A person to be examined is then requested to use the switches on the operation device 111 to search and select the name of the person himself or herself.

After this setting of the person to be examined, the controller 110 controls the searcher 106 in such a manner that the searcher 106 uses the person's name to search the database 105 for template data associated with the person to be examined currently. That is, the searcher 106 determines if or not there is template data associated with the person to be examined currently (step S32). If this determination reveals that there exists some desired template data in the database 105 (YES at step S32), the controller 110 controls the database 105 to have the desired template data sent to the cross-correlation processor 107 (step S33), before terminating this processing.

On the other hand, when the above determination shows that there is no desired template data in the database 105 (NO at step S32), the following actions will be taken.

First of all, the controller 110 prompts the person to grasp the steering wheel. When the person moves to grasp the steering wheel, the controller 110 detects such a grasp, and then controls both of the detector 101 and the amplifier 102 so that one frame of heartbeat signal is detected from the person to be examined and electrocardiogram waveform data is produced (step S34).

Then, the controller 110 monitors the electrocardiogram waveform data from the differentiating circuit 103, during which time the controller 110 determines whether or not an amount of noise included in the electrocardiogram waveform data is less than a given amount (that is, "noise determining processing").

This noise determining processing will now be described later, which gives estimation to the inquiry if there is noise or not.

If the controller 110 determines that there is much noise in the electrocardiogram waveform data, it is required to re-detect the heartbeat signal. Hence, the processing is returned to step S34, where the controller 110 again prompts the person to grasp the steering wheel, and controls both of the detector 101 and the amplifier 102 to detect one frame of heartbeat signal (step S35).

By contrast, when the controller 110 determines that there is less noise in the electrocardiogram waveform data, the controller 110 acts as follows.

The controller 110 makes the differentiating circuit 103 send out the electrocardiogram waveform data with less noise to the data waveform extractor 104. Then, the controller 110 gives a command to the data waveform extractor 104 so that the extractor 104 performs the foregoing representative waveform data producing processing (step S36).

Then the controller 110 gives a command to the searcher 106, so that the searcher 106 searches the database 105 on the basis of the representative waveform data (step S37). And the controller 110 determines based on searched results if or not there is template data having a high similarity to the representative waveform data (step S38). When it is determined that such similar template data is present in the database 105 (YES at step S38), the controller 110 makes the database 105 provide the cross-correlation processor 107 with the searched template data (step S39), before ending the present processing.

By the way, the determination whether or not there is template data with a high similarity to the representative waveform data can be performed with the use of a correlation value computed between representative waveform data and template data, as described before.

On the other hand, if the database 105 has no template data with a high similarity to the representative waveform data (NO at step S38), the controller 110 allows the searcher 106 to output the representative waveform data, as template data, to the cross-correlation calculator 107 (step S40), before ending the present processing.

Figure 9:
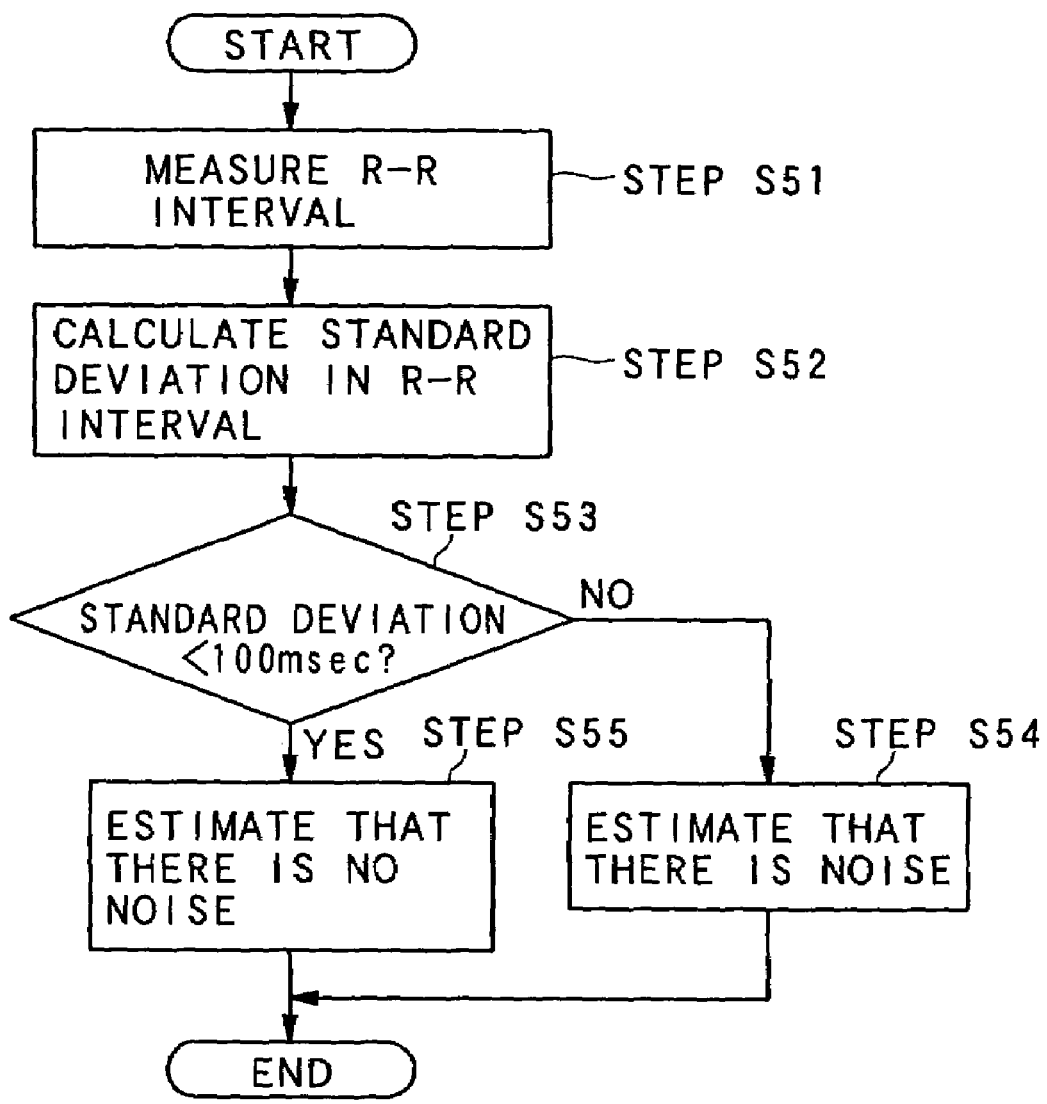
FIG. 9 is a flowchart showing the operation for noise determining processing in the first embodiment.

Referring to FIG. 9, the noise determining processing associated with the processing for setting template data, which is carried out by the controller 110, will now be described.

FIG. 9 is a flowchart showing the operations necessary for the noise determining processing for electrocardiogram waveform data.

In the present embodiment, electrocardiogram waveform data of which lower-frequency components have been removed by the differentiating circuit 103 is used. Hence, in performing the template processing, the controller 110 performs the noise determining processing directed to the electrocardiogram waveform data.

First, for performing the template setting processing, the controller 110 calculates each of R-R intervals in one frame of electrocardiogram waveform data outputted from the differentiating circuit 103 (step S51).

Then, using both of the value $x_n$ of each R-R interval defined by the equation (3) and an average $x_0$ of those values $x_n$, the controller 110 calculates a dispersion $\sigma^2$ and a standard deviation $\sigma$ (step S52).

$$\sigma^2 = \sum_{k=1}^{n}(x_k - \overline{x})^2 \Theta \overline{x} = \frac{1}{N}\sum_{k=1}^{n} x_k \qquad (3)$$

The controller 110 then moves to determination whether or not the calculated standard deviation $\sigma$ is smaller than 100 msec (step S53). If it has been determined that the standard deviation $\sigma$ is equal to or more than 100 msec (NO at step S53), the computer 110 estimates that there is noise in the electrocardiogram waveform data (step S54), before ending the processing. In contrast, when it has been found that that the standard deviation σ is less than 100 msec (YES at step S53), the computer 110 estimates that the electrocardiogram waveform data has hardly noise (step S55). Then the processing is ended.

As described above, the heart-rate measuring apparatus according to the present embodiment has, as one aspect thereof, the configuration provided with the database 105 in which one or more sets of template data of persons to be examined is stored in advance; the detector 101 detecting a heartbeat signal from a person to be examined; a combination of the amplifier 102 and the data waveform extractor 104 producing representative waveform data of the person based on the heartbeat signal; the searcher 106 searching the database 105 for template data for the person to be examined, on the basis of the representative waveform data produced by the data waveform extractor 104, the person being subjected to acquisition of the heartbeat signal; the cross-correlation processor 107 performing cross-correlation processing between the electrocardiogram waveform data produced by the amplifier 102 and the searched template data; the peak detection/calculating unit 108 calculating a maximum in each cardiac cycle (i.e., each heartbeat) of the cross-correlated electrocardiogram waveform data; and the heart rate calculator 109 calculating a heart rate using the maximums.

Accordingly, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Further, in the present embodiment, the detector 101 is configured such that it calculates correlation values correlated between the produced representative waveform data and template data stored in the database 105, and, based on the calculated correlation values, specify the template data of a person to be examined of which heartbeat signal has been acquired.

Thus, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In the present embodiment, there is provided another configuration, in which the data waveform extractor 104 cuts out waveform data lasting over each R-R interval, every heartbeat (i.e., every cardiac cycle), from the electrocardiogram waveform data produced by the amplifier 102, and then calculates one representative waveform data from the waveform data cut out every cardiac cycle. Responsively, the searcher 106 calculates correlation values correlated between the representative waveform data and the template data stored in the database 105, and then uses the calculated correlation values to specify template data associated with the person to be examined of which heartbeat signal has been acquired. In this case, the correlation values serve as information indicating a similarity between the representative waveform data and the template data.

This makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Still, in the present embodiment, in cases where it has been determined that each of correlation values between the representative waveform data and each of one or more sets of template data is smaller than a predetermined value, the controller 110 is able to specify the representative waveform data as template data to be searched.

This configuration makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment is based on the configuration, in which both the produced representative waveform data and the one or more sets to template data stored in the database 105 each include the name of a person to be examined to identify each waveform data from the other electrocardiogram waveform data. Additionally, the operation device 111 is provided to give the name of a person to be examined, to the representative waveform data, the name serving as identification information. In the database 105, one or more sets of template data have been stored with relevancy to the names of persons to be examined. The searcher 106 is configured to search the database 105 based on a person's name associated with the representative waveform data, in order to specify template data associated with the person to be examined of which heartbeat signal has been acquired.

This configuration also makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment results from a configuration, in which, while calculating a local maximum of electrocardiogram waveform data every one heartbeat (i.e., every one cardiac cycle), the peak detection/calculation unit 108 calculates a maximum (R wave) in each cardiac cycle, and then calculates a heart rate based on the maximums (R waves).

In consequence, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Incidentally, the above embodiment has been described about the heart-rate measuring apparatus 100 applied to the measurement of the heart rate of a human body, but this is not a sole application. This apparatus is usable in measuring a heart rate of an object other than the human body, such as creatures, as long as the object has the heart to pulsate.

In addition, the foregoing heart-rate measuring apparatus is formed into a dedicated heart-rate measuring apparatus. In place of this apparatus, a modified heart-rate measuring apparatus may be provided, in which the modified apparatus includes a computer and a recording medium. This recording medium can memorize a computer-readable program in which the foregoing heart-rate measurement algorithm is coded on a computer-readable language, while the computer can be configured to read in the program. Thus the similar action to the foregoing heart rate measurement can be obtained.

In such a heart-rate measuring apparatus capable of executing the heart-rate measurement program, a DVD or CD may be used as the recording medium. If such a recording medium is used, it is required to have a reading apparatus to read out the program from the recording medium.

Second Embodiment

Figure 10:
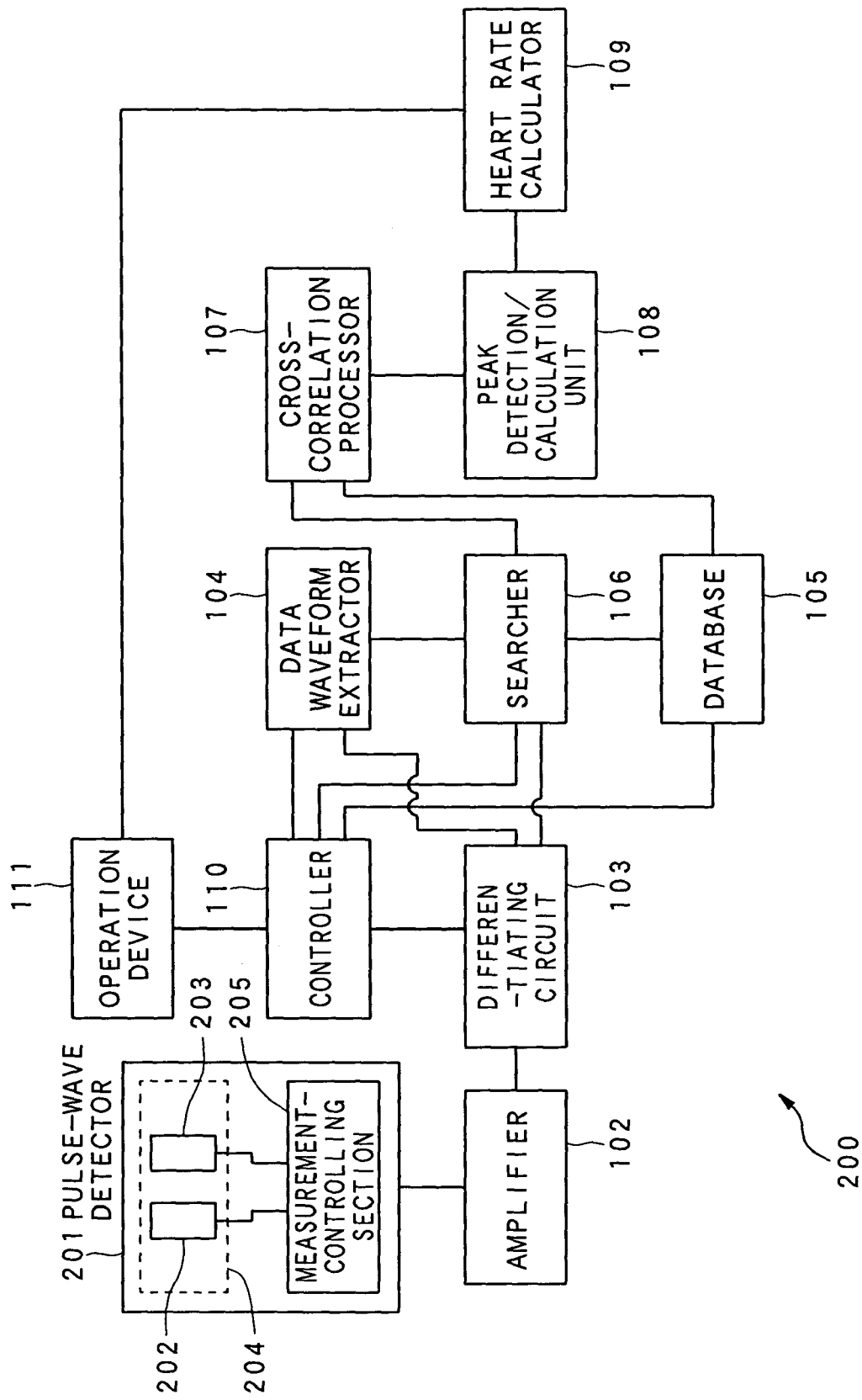
FIG. 10 is a block diagram showing the entire configuration of a heart rate measuring apparatus according to a second embodiment of the invention.

Referring to FIG. 10, a second embodiment of the heart-rate measuring apparatus according to the present application will now be described.

FIG. 10 shows the configuration of the heart-rate measuring apparatus used in this embodiment.

The present embodiment has a feature of using a pulse-wave detector 201 in the configuration shown in the first embodiment, instead of the detector to detect a heartbeat signal at a leg, arm or chest portion of the human body. The pulse-wave detector will detect a heartbeat signal through measuring the pulse wave generated at a portion of the human body. The remaining components and the heart-rate measurement operations are identical or similar to those in the first embodiment, so the identical components to those are referred by the same numerals and will be omitted from being described for the sake of a simplified explanation.

As shown in FIG. 10, a heart-rate measuring apparatus 200 according to the present embodiment is provided with a pulse-wave detector 201 detecting a heartbeat signal from a human body; a amplifier 102 producing electrocardiogram waveform data based on the detected heartbeat signal; a differentiating circuit 103 removing lower-frequency components from the produced electrocardiogram waveform data; a data waveform extractor 104 extracting a single representative waveform data from the produced electrocardiogram waveform data; a database 105 in which template data is stored in advance; a searcher 106 searching the database 105 for template data for an object to be examined or representative waveform data extracted based on electrocardiogram waveform data acquired from the object; a cross-correlation processor 107 performing cross-correlation processing between the produced electrocardiogram waveform data and the searched template data or the extracted template data; a peak detection/calculating unit 108 detecting, from the cross-correlated electrocardiogram waveform data, each R wave showing a peak value appearing every heartbeat and calculating an interval between two R waves (R-R interval); a heart rate calculator 109 calculating a heart rate using the calculated R-R intervals; a controller 110 controlling each component in this apparatus as well as determining whether or not the produced electrocardiogram waveform data has noise components; and an operation device 111 used for operating each necessary components arranged in this apparatus.

The pulse-wave detector 201, of which sensing portion is applied to a person to be examined such that, for instance, any of person's fingers is inserted into the sensing portion or either of person's earlobes is clipped by the sensing portion, has the capability of detecting and measuring the pulse wave from the person to be examined. Practically, the pulse-wave detector 201 has a measurement section (sensing portion) 204 provided with an illumination element 202 illuminating an infrared ray and a light-reception element 203 receiving the reflected light of the infrared ray and a measurement-controlling section 205 controlling the operations of the measurement section 204.

The illumination element 202 is in charge of radiating the infrared ray onto the inserted finger or the clipped earlobe, while the light-reception element 203 is responsible for detecting the reflected infrared ray from the inserted finger or the clipped earlobe.

The measurement-controlling section 205 computes a reflection rate of the reflected infrared ray detected by the light-reception element 203, and creates a heartbeat signal based on the computed reflection rate. The heartbeat signal is sent to the amplifier 102.

In addition, the amplifier 102 operates in a similar way to that in the first embodiment, in which the amplifier 102 produces electrocardiogram waveform data using the inputted heartbeat signal.

As described above, the heart-rate measuring apparatus according to the present embodiment has, as one aspect thereof, the configuration provided with the database 105 in which one or more sets of template data of persons to be examined is stored in advance; the pulse-wave detector 201 detecting a heartbeat signal from a person to be examined; a combination of the amplifier 102 and the data waveform extractor 104 producing representative waveform data of the person based on the heartbeat signal; the searcher 106 searching the database 105 for template data for the person to be examined, on the basis of the representative waveform data produced by the data waveform extractor 104, the person being subjected to acquisition of the heartbeat signal; the cross-correlation processor 107 performing cross-correlation processing between the electrocardiogram waveform data produced by the amplifier 102 and the searched template data; the peak detection/calculating unit 108 calculating a maximum in each cardiac cycle (i.e., each heartbeat) of the cross-correlated electrocardiogram waveform data; and the heart rate calculator 109 calculating a heart rate using the maximums.

Accordingly, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Further, in the present embodiment, the pulse-wave detector 201 is configured such that it calculates correlation values correlated between the produced representative waveform data and template data stored in the database 105, and, based on the calculated correlation values, specify the template data of a person to be examined of which heartbeat signal has been acquired.

Thus, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In the present embodiment, there is provided another configuration, in which the data waveform extractor 104 cuts out waveform data lasting over each R-R interval, every heartbeat (i.e., every cardiac cycle), from the electrocardiogram waveform data produced by the amplifier 102, and then calculates one representative waveform data from the waveform data cut out every cardiac cycle. Responsively, the searcher 106 calculates correlation values correlated between the representative waveform data and the template data stored in the database 105, and then uses the calculated correlation values to specify template data associated with the person to be examined of which heartbeat signal has been acquired. In this case, the correlation values serve as information indicating a similarity between the representative waveform data and the template data.

This makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Still, in the present embodiment, in cases where it has been determined that each of correlation values between the representative waveform data and each of one or more sets of template data is smaller than a predetermined value, the controller 110 is able to specify the representative waveform data as template data to be searched.

This configuration makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment is based on the configuration, in which both the produced representative waveform data and the one or more sets to template data stored in the database 105 each include the name of a person to be examined to identify each waveform data from the other electrocardiogram waveform data. Additionally, the operation device 111 is provided to give the name of a person to be examined, to the representative waveform data, the name serving as identification information. In the database 105, one or more sets of template data have been stored with relevancy to the names of persons to be examined. The searcher 106 is configured to search the database 105 based on a person's name associated with the representative waveform data, in order to specify template data associated with the person to be examined of which heartbeat signal has been acquired.

This configuration also makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment results from a configuration, in which, while calculating a local maximum of electrocardiogram waveform data every one heartbeat (i.e., every one cardiac cycle), the peak detection/calculation unit 108 calculates a maximum (R wave) in each cardiac cycle, and then calculates a heart rate based on the maximums (R waves).

In consequence, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Incidentally, the above embodiment has been described about the heart-rate measuring apparatus 200 applied to the measurement of the heart rate of a human body, but this is not a sole application. This apparatus is usable in measuring a heart rate of an object other than the human body, such as creatures, as long as the object has the heart to pulsate.

In addition, the foregoing heart-rate measuring apparatus is formed into a dedicated heart-rate measuring apparatus. In place of this apparatus, a modified heart-rate measuring apparatus may be provided, in which the modified apparatus includes a computer and a recording medium. This recording medium can memorize a computer-readable program in which the foregoing heart-rate measurement algorithm is coded on a computer-readable language, while the computer can be configured to read in the program. Thus the similar action to the foregoing heart rate measurement can be obtained.

In such a heart-rate measuring apparatus capable of executing the heart-rate measurement program, a DVD or CD may be used as the recording medium. If such a recording medium is used, it is required to have a reading apparatus to read out the program from the recording medium.

Third Embodiment

Figure 11:
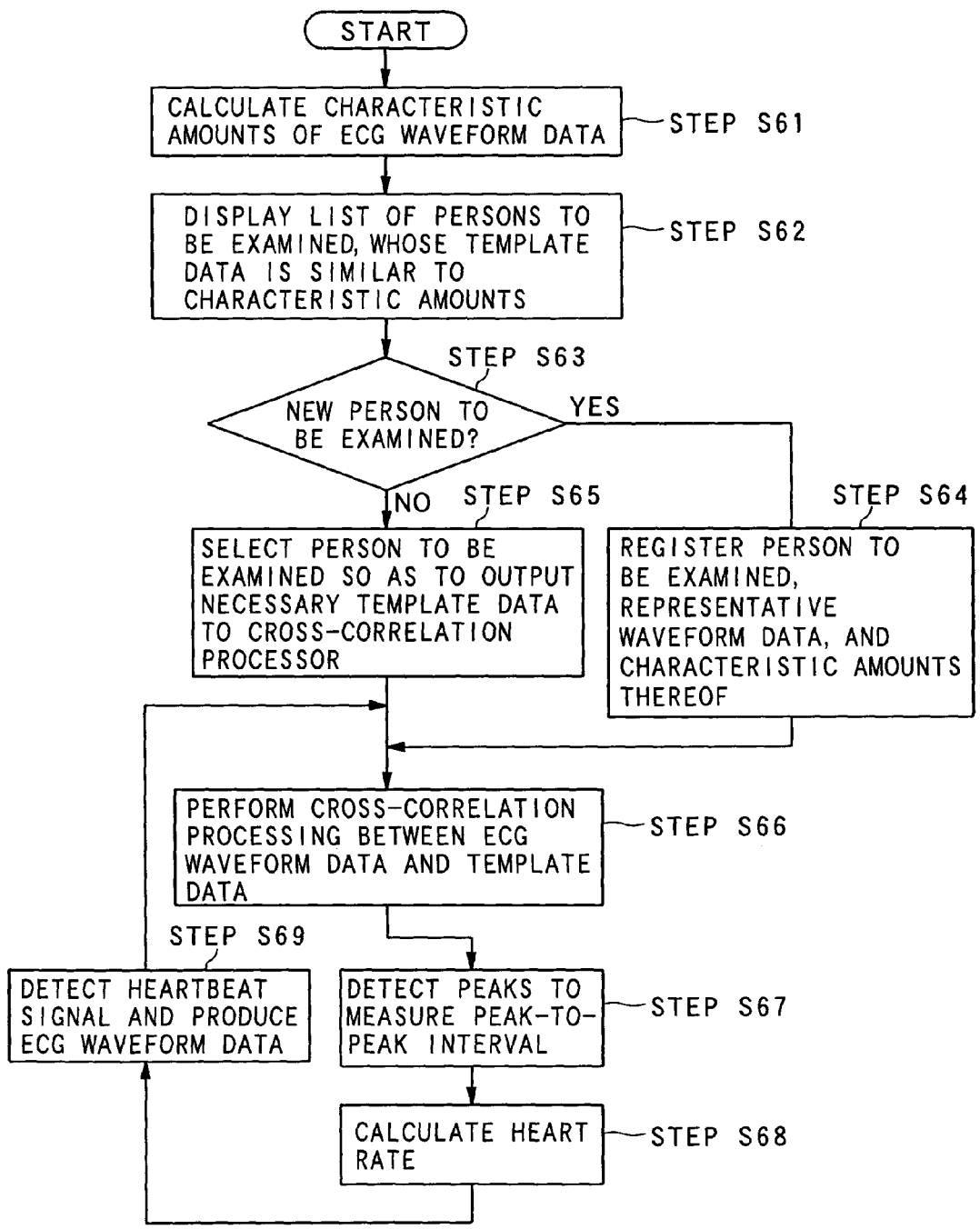
FIG. 11 is a flowchart explaining the heart-rate measurement operation carried out in the third embodiment.
Figure 12:
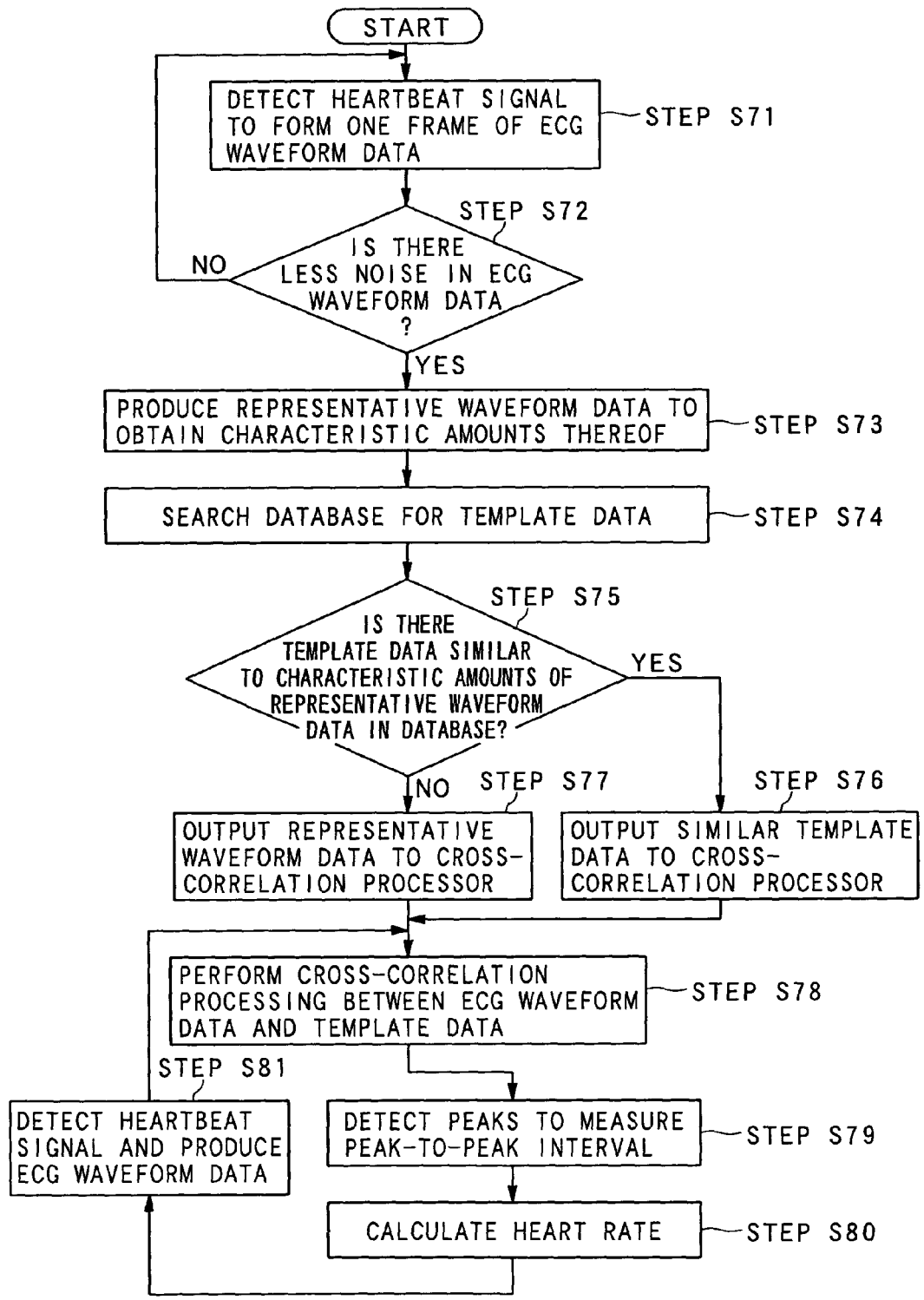
FIG. 12 is a flowchart explaining the heart-rate measurement operation carried out in a modification from the third embodiment.

Referring to FIGS. 11 and 12, a third embodiment of the heart-rate measuring apparatus according to the present invention will now be described.

The present embodiment features the configuration of searching the database for specifying template data with the use of amounts that are characteristic of representative waveform data used as electrocardiogram waveform data. This configuration is carried out in the first embodiment, in place of the configuration in which names of persons to be examined are adopted as identification information and the database is searched for specifying template data by using a person's name.

In the present embodiment, the characteristic amounts in representative waveform data consist of an amount indicating an interval of time between the P and Q waves (hereinafter referred to as "PQ interval"), a "QRS width", and an amount indicating an interval of time between the Q and T waves (hereinafter referred to as "QT interval").

These amounts of PQ interval, QRS width, and QT interval are unchangeable in their characteristics even when the heart rate change, thus being inherent to individuals and being usable in distinguishing each individual person from the others.

Usually, the PQ interval is in a range of 0.12 to 0.20 sec., the QRS width is in a range of 0.06 to 0.10 sec., and the QT interval falls into a range of 0.30 to 0.45 sec, respectively. Combining these amounts with each other allows each person to be distinguished from the others.

The database 105 according to the present embodiment is configured to memorize, in addition to one or more sets of template data, the PQ interval, QRS width, and QT interval which are calculated from each set of the template data, correspondingly to each set of template data.

The data waveform extractor 104 acquires these PQ interval, QRS width, and QT interval from the representative waveform data, while the searcher 106 searches the database 105 for template data that is consistent with the acquired PQ interval, QRS width, and QT interval in cases where the database 105 is subjected to a search conducted based on the representative waveform data.

To be specific, in the present embodiment, in performing the individual authentication, the searcher 106 draws a comparison between the characteristic amounts in the representative waveform data and those of each set of template data stored in the database 105, and provides a list of one or more persons to be examined, the characteristic amounts in whose template data are closer in a similarity to those of the representative waveform data.

For instance, the searcher 106 calculates each of the characteristic amounts, that is, the PQ interval, QRS width, and QT interval, in representative waveform data that has been given. Then, the searcher 106 proceeds to calculation of an error $e_n$ carried out on the following formula (4) every set of template data with the use of the characteristic amounts (the PQ interval, QRS width, and QT interval).

$$e_0 > e_n = |(PQ_n-PQ)/PQ_n| \times |(QRS_n-QRS)/QRS_n| \times |(QT_n-QT)/QT_n| (n=1, 2, \ldots, k) \quad (4),$$

in which $PQ_0$, $QRS_0$ and $QT_0$ denote the characteristic amounts in the representative waveform data which is currently used and $PQ_n$, $QRS_n$ and $QT_n$ denote the characteristic amounts in each set of template data stored in the database 105.

Furthermore, the searcher 106 is configured to determine whether or not there are one or more sets of template data in the database 105 by comparing each error en with a predetermined threshold $e_0$. Concerning this, a configuration is made such that if there is template data of which error $e_n$ is less than the threshold $e_0$, the template data is considered to be one having a high similarity, thus providing such template data to a not-shown display portion.

In general, the error $e_0$ that serves as the threshold is preferably 0.01 or less. Thus, a configuration is made such that, in the case that each of a plurality of sets of template data shows the error $e_n$ equal to or less than 0.01, the names of persons to be examined, who provide the plural sets of template data, are given in the form of a list.

In addition, the present embodiment includes other configurations as follows. When the template data is given by a not-shown display portion, the names of persons to be examined associated with one or more sets of template data are displayed on the display portion, as will be described later. Still, when one set of template is selected among the displayed sets of template data in response to a command issued by the operation device 111, the searcher 106 outputs the selected template data to the cross-correlation processor 107.

By way of example, the searcher 106 of this embodiment constitutes the setting averages according to the present embodiment.

With reference to FIG. 11, the operation for detecting a heart rate in the present embodiment will now be descried.

FIG. 11 shows a flowchart for the heart-rate measurement operation carried out in the present embodiment.

When a person to be examined operates the operation device 111 to instruct the controller 110 to start the heart-rate measurement operation, the controller 110 responds to this instruction by persuading the person to grasp a steering wheel. Responsively to the person's grasp of the steering wheel, the controller 110 controls both the detector 110 and the amplifier 102 so that they detect a heartbeat signal for producing one frame of electrocardiogram waveform data and calculate the characteristic amounts in the electrocardiogram waveform data (step S61).

The calculation of such characteristic amounts will now be described. The controller 110 has the produced electrocardiogram waveform data sent to the data waveform extractor 104 via the differentiating circuit 103. Then the controller 110 gives a control command to the data waveform extractor 104 so as to enable the extractor 104 to perform the processing for producing representative waveform data, with the result that the characteristic amounts in the representative waveform data, i.e., the PQ interval, QRS width, and QT interval, are figured out.

In this case, the electrocardiogram waveform data is produced, which is followed by calculation of the characteristic amounts in the electrocardiogram waveform data. Alternatively, the characteristic amounts in electrocardiogram waveform data may be figured out directly, without producing the electrocardiogram waveform data.

The controller 110 then controls the searcher 106 so that the searcher 106 uses the characteristic amounts to search the database 105 in search of template data similar to the characteristic amounts in the representative waveform data. Under the control of the controller 110, the names of persons to be examined associated with such similar template data are displayed as a list on the display portion (not shown) arranged on the operation device 111 (step S62).

The controller 110 then urges the person to be examined to select whether the person of which heartbeat signal has been detected is either a new person to be examined or one of the persons presented by the list on the not-shown display portion (step S63). If the selection through the operation device 111 is made to point out the new person to be examined, the controller 110 will allow the currently handled representative waveform data, the characteristic amounts thereof, and the names of the persons to be examined to be registered into the database 105, and allow the representative waveform data to be sent to the cross-correlation processor 107 (step S64).

In cases where the representative waveform data is registered into the database 105, the controller 110 prompts the person to register the person's name by using the operation device 111.

On the other hand, if any of the names of the persons to be examined is selected on the list displayed by the display portion of the operation device 111, the template data associated with the selected person's name is outputted from the database 105 to the cross-correlation processor 107 (step S65).

The controller 110 then performs the cross-correlation processor 107 so that the processor 107 performs the cross-correlation processing between the template data specified through the template setting processing and the electrocardiogram waveform data sent from the differentiating circuit 103 (step S66).

Then, the controller 110 proceeds to the next step, where the cross-correlated electrocardiogram waveform data is sent to the peak detection/calculation unit 108. By this unit 108, an R wave is detected every cardiac cycle, i.e., every one heartbeat, and a peak-to-peak interval from each peak to the next peak is calculated, thus a peak-to-peak interval value being provided (step S67).

Then, the controller 110 controls the heart rate calculator 109 so that it calculates a reciprocal of the peak-to-peak interval, multiplies the reciprocal by 60 to figure out a heart rate, and outputs the calculated heart rate to the operation device 111 or to an externally placed unit (step S68).

The controller 110 further prompts the person to be examined to grasp the steering wheel, makes the detector 101 detect a heartbeat signal, and makes the amplifier 102 produce electrocardiogram waveform data. The controller 110 allows the electrocardiogram waveform data to be sent to the differentiating circuit 103, where lower-frequency components of the data are removed, and the resultant electrocardiogram waveform data is provided to the cross-correlation processor 107 (step S69). Then the processing is handed over to step S66 to repeat the processes at steps S66 to S68.

In the present processing, once being started, the heart-rate measurement operations are repeated, as a basic mode, every specified period of time through the performance of the processes at steps S66 to S69. In consequence, every specified period of time, the heart rate is calculated in a repeated manner, and sent to the display portion of the operation device 111 or an external device.

As described above, the heart-rate measuring apparatus according to the present embodiment has, as one aspect thereof, the configuration provided with the database 105 in which one or more sets of template data of persons to be examined is stored in advance; the detector 101 detecting a heartbeat signal from a person to be examined; a combination of the amplifier 102 and the data waveform extractor 104 producing representative waveform data of the person based on the heartbeat signal; the searcher 106 searching the database 105 for template data for the person to be examined, on the basis of the representative waveform data produced by the data waveform extractor 104, the person being subjected to acquisition of the heartbeat signal; the cross-correlation processor 107 performing cross-correlation processing between the electrocardiogram waveform data produced by the amplifier 102 and the searched template data; the peak detection/calculating unit 108 calculating a maximum in each cardiac cycle (i.e., each heartbeat) of the cross-correlated electrocardiogram waveform data; and the heart rate calculator 109 calculating a heart rate using the maximums.

Accordingly, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Further, in the present embodiment, the detector 101 is configured such that it draws a comparison in the characteristic amounts (i.e., the PQ interval, QRS width, and QT interval) between the produced representative waveform data and each set of template data stored in the database 105 so that each similarity therebetween is calculated, and then, based on the calculated similarities, specify the template data of a person to be examined of which heartbeat signal has been acquired.

Thus, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In the present embodiment, there is provided another configuration, in which the data waveform extractor 104 cuts out waveform data lasting over each R-R interval, every heartbeat (i.e., every cardiac cycle), from the electrocardiogram waveform data produced by the amplifier 102, and then calculates one representative waveform data from the waveform data cut out every cardiac cycle. Responsively, the searcher 106 calculates similarities between the representative waveform data and each set of template data stored in the database 105, and then uses the calculated similarities to specify template data associated with the person to be examined of which heartbeat signal has been acquired.

This makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In the present invention, the produced representative waveform data and each set of template data stored in the database 105, respectively, include pieces of identification information (i.e., the characteristic amounts consisting of the PQ interval, QRS width, and QT interval) to be distinguished from the other electrocardiogram waveform data. To make use of such pieces of identification information, the searcher 106 is provided to set the name of a person to be examined (which also functions as identification information) to the representative waveform data, while the database 105 is provided to memorize each set of template data associated with the characteristics amounts (i.e., identification information) of the electrocardiogram waveform data. Thus, the searcher 106 uses the characteristic amounts in the representative waveform data to search the database 105 to specify the template data associated with the person to be examined who has been subjected to the acquisition of the heartbeat signal.

Accordingly, a necessary template data can be specified using the name of a person to be examined. This configuration therefore makes it possible to appropriately enhance the peaks of electrocardiogram waveform data produced from a heartbeat signal detected from the person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment results from a configuration, in which, while calculating a local maximum of electrocardiogram waveform data every one heartbeat (i.e., every one cardiac cycle), the peak detection/calculation unit 108 calculates a maximum (R wave) in each cardiac cycle, and then calculates a heart rate based on the maximums (R waves).

In consequence, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Incidentally, the above embodiment has been described about the heart-rate measuring apparatus applied to the measurement of the heart rate of a human body, but this is not a sole application. This apparatus is usable in measuring a heart rate of an object other than the human body, such as creatures, as long as the object has the heart to pulsate.

There is a modification about how to specify a person to be examined who is subjected to measurement of the heart rate. In the above embodiment, such specification has been carried out based on one or more sets of template data of which characteristic amounts are similar to those of a certain set of electrocardiogram waveform data. Such one or more sets of similar template data are listed up for selection conducted by a person to be examined, so that the selection will lead to the specification. The modification is to, like the first embodiment, perform the noise determining processing to allow the template data to be set automatically.

The heart rate measurement based on this modification will now be described in connection with FIG. 12.

FIG. 12 is a flowchart showing the operation for the heart rate measurement.

When a person to be examined operates the operation device 111 to instruct the controller 110 to start the heart-rate measurement operation, the controller 110 responds to this instruction by persuading the person to grasp a steering wheel. Responsively to the person's grasp of the steering wheel, the controller 110 controls both the detector 110 and the amplifier 102 so that they detect a heartbeat signal for producing one frame of electrocardiogram waveform data (step S71).

The controller 110 then monitors the electrocardiogram waveform data outputted from the differentiating circuit 103 in order to determine whether or not there is less noise in this electrocardiogram waveform data (i.e., noise determining processing; step S72). If the controller 110 determines that there is much noise in the electrocardiogram waveform data, it is required to re-detect the heartbeat signal. Hence, the processing is returned to step S71, where the controller 110 again prompts the person to grasp the steering wheel, and controls both of the detector 101 and the amplifier 102 to detect one frame of heartbeat signal.

This noise determining processing is done in the similar way to that in the first embodiment.

Meanwhile, when determining that there is less noise in the electrocardiogram waveform data, the controller 110 will act as follows.

The controller 110 makes the differentiating circuit 103 send out the electrocardiogram waveform data with less noise to the data waveform extractor 104. Then, the controller 110 gives a command to the data waveform extractor 104 so that the extractor 104 performs the foregoing representative waveform data producing processing, and calculates the characteristic amounts (that is, the PQ interval, QRS width, and QT interval) of the representative waveform data (step S73).

Then the controller 110 gives a command to the searcher 106, so that the searcher 106 searches the database 105 on the basis of the characteristic amounts in the representative waveform data (step S74). And the controller 110 determines based on searched results if or not there is template data of which characteristic amounts are similar to those of the representative waveform data (step S75). When it is determined that such similar template data is present in the database 105 (YES at step S75), the controller 110 makes the database 105 provide the cross-correlation processor 107 with the searched template data (step S76).

By the way, the determination whether or not there is template data similar to the representative waveform data can be performed with the use of the characteristic amounts (functioning as a value indicating the similarity) of electrocardiogram waveform data.

On the other hand, if the database 105 has no template data similar to the representative waveform data (NO at step S75), the controller 110 allows the searcher 106 to output the representative waveform data, as template data, to the cross-correlation calculator 107 (step S77).

The controller 110 then performs the cross-correlation processor 107 so that the processor 107 performs the cross-correlation processing between the specified template data and the electrocardiogram waveform data sent from the differentiating circuit 103 (step S78).

Then, the controller 110 proceeds to the next step, where the cross-correlated electrocardiogram waveform data is sent to the peak detection/calculation unit 108. By this unit 108, an R wave is detected every frame, and a peak-to-peak interval from each peak to the next peak is calculated, thus a peak-to-peak interval value being provided (step S79).

Then, the controller 110 controls the heart rate calculator 109 so that it calculates a reciprocal of the peak-to-peak interval, multiplies the reciprocal by 60 to figure out a heart rate, and outputs the calculated heart rate to the operation device 111 or to an externally placed unit (step S80).

The controller 110 further prompts the person to be examined to grasp the steering wheel, makes the detector 101 detect a heartbeat signal, and makes the amplifier 102 produce electrocardiogram waveform data. The controller 110 allows the electrocardiogram waveform data to be sent to the differentiating circuit 103, where lower-frequency components of the data are removed, and the resultant electrocardiogram waveform data is provided to the cross-correlation processor 107 (step S81). Then the processing is handed over to step S78 to repeat the processes at steps S78 to S80.

In the present processing, once being started, the heart-rate measurement operations are repeated, as a basic mode, every specified period of time through the performance of the processes at steps S78 to S81. In consequence, every specified period of time, the heart rate is calculated in a repeated manner, and sent to the display portion of the operation device 111 or an external device.

As described above, the controller 110 gives various control commands to the necessary components in order to establish the heart-rate measurement operations.

In addition, the foregoing heart-rate measuring apparatus is formed into a dedicated heart-rate measuring apparatus. In place of this apparatus, a modified heart-rate measuring apparatus may be provided, in which the modified apparatus includes a computer and a recording medium. This recording medium can memorize a computer-readable program in which the foregoing heart-rate measurement algorithm is coded on a computer-readable language, while the computer can be configured to read in the program. Thus the similar action to the foregoing heart rate measurement can be obtained.

In such a heart-rate measuring apparatus capable of executing the heart-rate measurement program, a DVD or CD may be used as the recording medium. If such a recording medium is used, it is required to have a reading apparatus to read out the program from the recording medium.

Fourth Embodiment

Referring to FIG. 13, a fourth embodiment of the present invention will now be described. This embodiment concerns a reproduction control apparatus.

An apparatus according to the present embodiment is modified from that described in the first embodiment. Practically, instead of the configuration where all the components such as the detector and amplifier are packed into one apparatus, the apparatus according to the fourth embodiment is equipped with a terminal and a server. Of these, the terminal includes the detector 101 detecting a heartbeat signal and the operation device 111 with which necessary operations for the heart rate measurement are done. The server is provided with the remaining components including the database 105 in which electrocardiogram waveform data is stored previously, the searcher 106 searching the database 105, and the cross-correlation processor 107 and heart-rate calculator 109 both of which are used for calculating a heart rate. This divided construction features the fourth embodiment. Each component in the fourth embodiment is constructed in the same way as that in the first embodiment, thus being assigned to the numerals which are the same as those in the first embodiment, thus being omitted from detail explanations.

The heart-rate measurement operations in the present embodiment are the same as those in the first embodiment, except for commands issued from the operation device of the terminal are transmitted to individual components of the server via a controller placed in the server and information showing a heart rate calculated in the server is transmitted to the terminal. Hence, for the sake of a simplified explanation, the heart-rate measurement operations are omitted from being explained.

FIG. 13 is a block diagram showing the configuration of a heart-rate measuring system according to the present embodiment.

As shown in FIG. 13, the heart-rate measuring system 300 according to the present embodiment is equipped with a terminal 310 mounted on a moving apparatus such as vehicle and a server 320 fixedly mounted at an arbitrarily selected location. Both of the terminal 310 and the server 320 are communicably connected to each other via a wireless or wired electrical communication line.

As shown in FIG. 13, the terminal 310 is provided with the detector 101 detecting a heartbeat signal from a person to be examined, a transmitter 311 transmitting the detected heartbeat signal to the server 320, a receiver 312 receiving information indicative of a measured heart rate, a controller 313 controlling necessary components in the terminal 310, and an operation device 314 operated for entering various types of information to the terminal 310.

Both of the transmitter 311 and the receiver 312 are in charge of transmission and reception, via antennas AT, of the heartbeat signal, the information about the heart rate (hereinafter referred to as "heart rate information"), and signals indicating the operations done with the terminal 310 by a person to be examined (hereinafter referred to as "operation command signal").

The operation device 314 is configured such that, like that in the first embodiment, by way of example, the device has a plurality of switches and a display portion (not shown). Thus, an operator is able to select and specify a person to be examined, while viewing the screen on the display portion.

Command signals from the operation device 314, which are formed on contents selected and specified by a person to be examined, are transmitted to the server 320 via the transmitter 311.

On the other hand, the server 320 is provided with, as shown in FIG. 13, a receiver 321 receiving both the heartbeat signal and the operation command signal that have been transmitted from the terminal 310, a amplifier 102 producing electrocardiogram waveform data based on the received heartbeat signal; a differentiating circuit 103 removing lower-frequency components from the produced electrocardiogram waveform data; a data waveform extractor 104 extracting a single representative waveform data from the produced electrocardiogram waveform data; a database 105 in which a plurality of template data is stored in advance; a searcher 106 searching the database 105 for template data for an object to be examined or representative waveform data extracted based in electrocardiogram waveform data acquired from the object; a cross-correlation processor 107 performing cross-correlation processing between the produced electrocardiogram waveform data and the searched template data or the extracted template data; a peak detection/calculating unit 108 detecting, from the cross-correlated electrocardiogram waveform data, each R wave showing a peak value appearing every heartbeat, that is, appearing within each cardiac cycle, indicating periodically repeated movements and calculating an interval between two R waves; a heart rate calculator 109 calculating a heart rate using the calculated R-R intervals; a transmitter 322 transmitting the obtained heart rate information to the terminal 310; and a controller 323 controlling each component in this server on the basis of the command signals coming from the terminal 310 as well as determining whether or not the produced electrocardiogram waveform data has noise components.

By way of example, the receiver 321 corresponds to the acquisition unit according to the present invention and the controller 323 corresponds to the setting unit according to the present invention.

In the similar way to the terminal 310, both of the receiver 321 and the transmitter 322 have the capability of transmitting and receiving the heartbeat signal, heart rate signal, and operation command signal to and from the terminal 310 via the antennas AT.

Accordingly, in the present embodiment, the heart-rate measuring apparatus according to the present embodiment has, as one aspect thereof, the configuration provided with the database 105 in which one or more sets of template data of persons to be examined is stored in advance; the detector 101 detecting a heartbeat signal from a person to be examined; a combination of the amplifier 102 and the data waveform extractor 104 producing representative waveform data of the person based on the heartbeat signal; the searcher 106 searching the database 105 for template data for the person to be examined, on the basis of the representative waveform data produced by the data waveform extractor 104, the person being subjected to acquisition of the heartbeat signal; the cross-correlation processor 107 performing cross-correlation processing between the electrocardiogram waveform data produced by the amplifier 102 and the searched template data; the peak detection/calculating unit 108 calculating a maximum in each cardiac cycle (i.e., each heartbeat) of the cross-correlated electrocardiogram waveform data; and the heart rate calculator 109 calculating a heart rate using the maximums.

Accordingly, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Further, in the present embodiment, the detector 101 is configured such that it calculates correlation values correlated between the produced representative waveform data and template data stored in the database 105, and, based on the calculated correlation values, specify the template data of a person to be examined of which heartbeat signal has been acquired.

Thus, it is possible to not only adequately enhance the peaks in the electrocardiogram waveform data produced from the heartbeat signal acquired from a person to be examined but also, on an individual basis, optimize the data from which a heart rate is figured out. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

In the present embodiment, there is provided another configuration, in which the data waveform extractor 104 cuts out waveform data lasting over each R-R interval, every heartbeat (i.e., every cardiac cycle), from the electrocardiogram waveform data produced by the amplifier 102, and then calculates one representative waveform data from the waveform data cut out every cardiac cycle. Responsively, the searcher 106 calculates correlation values correlated between the representative waveform data and the template data stored in the database 105, and then uses the calculated correlation values to specify template data associated with the person to be examined of which heartbeat signal has been acquired. In this case, the correlation values serve as information indicating a similarity between the representative waveform data and the template data.

This makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Still, in the present embodiment, in cases where it has been determined that each of correlation values between the representative waveform data and each of one or more sets of template data is smaller than a predetermined value, the controller 110 is able to specify the representative waveform data as template data to be searched.

This configuration makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment is based on the configuration, in which both the produced representative waveform data and the one or more sets of template data stored in the database 105 each include the name of a person to be examined to identify each waveform data from the other electrocardiogram waveform data. Additionally, the operation device 111 is provided to give the name of a person to be examined, to the representative waveform data, the name serving as identification information. In the database 105, one or more sets of template data have been stored with relevancy to the names of persons to be examined. The searcher 106 is configured to search the database 105 based on a person's name associated with the representative waveform data, in order to specify template data associated with the person to be examined of which heartbeat signal has been acquired.

This configuration also makes it possible to appropriately enhance the peaks of electrocardiogram waveform data produced from a heartbeat signal detected from a person to be examined. Concurrently, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

Another aspect of the present embodiment results from a configuration, in which, while calculating a local maximum of electrocardiogram waveform data every one heartbeat (i.e., every one cardiac cycle), the peak detection/calculation unit 108 calculates a maximum (R wave) in each cardiac cycle, and then calculates a heart rate based on the maximums (R waves).

In consequence, the data from which a heart rate is computed can be optimized person by person. Hence, even when there is body motion during detection of a heartbeat signal from the human to be examined and/or there is contact resistance intervening in a detecting path of the heartbeat signal, noise caused in electrocardiogram waveform data can easily be removed from the data or greatly suppressed in the data, thereby providing a heart-rate measuring apparatus with higher detection accuracy.

There can also be provided some modifications in the present embodiment. Instead of the detector attached to the steering wheel of a vehicle, the pulse-wave detector described in the second embodiment can be adopted.

Another modification is concerned with the search of template data in the database. The present embodiment adopts the same search way as that in the first embodiment, where the name of a person to be examined and correlation values between a set of representative waveform data and each set of template data are used for the search. Alternatively, like the second embodiment, the characteristic amounts in electrocardiogram waveform data can be used for such search. In such a configuration, the operations for measuring a heart rate can be done in the similar manner to that in the second embodiment.

For the sake of completeness, it should be mentioned that the embodiments and modifications thereof explained so far are not definitive lists of possible embodiments of the present invention. The expert will appreciate that it is possible to combine the various construction details or to supplement or modify them by measures known from the prior art without departing from the basic inventive principle.

The entire disclosure of Japanese Patent Application No. 2002-252447 filed on Aug. 30, 2002 including the specification, claims, drawings and summary is incorporated herein by reference in its entirety.

What is claimed is:

1. A system for measuring a heart rate, comprising:
a database in which at least one set of electrocardiogram waveform data of a living body related to each person to be examined are stored in advance, the electrocardiogram waveform data serving as reference waveform data;
an acquisition unit for acquiring a heartbeat signal generated in the living body;
a production unit for producing electrocardiogram waveform data of the living body based on the acquired heartbeat signal;
a search unit for searching the database on the basis of produced waveform data served by the produced electrocardiogram waveform data, to specify the reference waveform data of the living body from which the heartbeat signal has been acquired;
a cross-correlation processing unit for performing cross-correlation processing between the produced waveform data of which lower-frequency components have been removed and the specified reference waveform data; and
a calculation unit for calculating an extremal value every period of time from data subjected to $R_{xy}$ in the cross-correlation processing and the heart rate based on the extremal value calculated every period of time,
wherein the cross-correlation processing unit calculates $R_{xy}$ defined by the equation (1) every time the delay time $\tau$ is shifted by a predetermined amount:

$$R_{xy}(t) = \lim_{T \to 0} \frac{1}{T} \int_{\frac{T}{2}}^{\frac{T}{2}} x(t) y(t + \tau) dt, \quad (1)$$

where x denotes the produced electrocardiogram waveform data of which lower-frequency components have been removed, y denotes the specified reference waveform data template data, $\tau$ denotes a delay time and provides a value of the $R_{xy}$ to the calculation unit.

2. The system according to claim 1, wherein the search unit comprises:
a similarity calculating unit for calculating a similarity between the produced waveform data produced by the production unit and each set of the reference waveform data stored in the database; and
a waveform data specifying unit for specifying, based on the calculated similarity, the reference waveform data of the living body from which the heartbeat signal has been acquired.

3. The system according to claim 2, wherein the similarity calculating unit comprises:
a waveform cutting-out element for cutting out, every predetermined period of time, waveform data from the produced waveform data produced by the production unit;
an average calculating element for calculating a single average waveform data based on the waveform data cut out every period of time; and
a data similarity calculating element for calculating the similarity between the average waveform data and each set of the reference waveform data stored in the database,
wherein the waveform data specifying unit is configured to specify, based on the calculated similarity, the reference waveform data of the living body from which the heartbeat signal has been acquired.

4. The system according to claim 3, wherein the waveform data specifying unit is configured to specify the average waveform data as being the reference waveform data, in cases where the similarity calculating unit determines that the similarity between the average waveform data and each set of the reference waveform data stored in the database is less than a predetermined value.

5. The system according to claim 1, wherein the electrocardiogram waveform data produced as the produced waveform data by the production unit and each set of electrocardiogram waveform data stored as the reference waveform data in the database include identification information distinguishable from the other electrocardiogram waveform data, respectively;

the system is configured to further comprises a setting unit configured to set identification information to the produced waveform data produced by the production unit;

the database is configured to store therein the reference waveform data so as to relate to identification information inherent to the living body; and the search unit is configured to search the database based on the indentation information of the produced waveform data, to specify the reference waveform data of the living body from which the heartbeat signal has been acquired.

6. The system according to claim 5, wherein the identification information includes at least one of a name showing the living body and a characteristic amount in each set of electrocardiogram waveform information;

the database is configured to store therein the reference waveform data made to relate to at least one of the name of the living body and the characteristic amount in the reference waveform data; and the setting unit is configured to set, as the identification information, at least one of the name of the living body and the characteristic amount in the reference waveform data.

7. The system according to claim 1, wherein the calculation unit is configured to calculate a local maximum between every predetermined area and to calculate the heart rate based on the local maximum.

8. A method of measuring a heart rate, comprising:

a acquiring process of acquiring a heartbeat signal generated in a living body;

a producing process of producing electrocardiogram waveform data of the living body based on the acquired heartbeat signal;

a searching process of searching a database in which at least one set of electrocardiogram waveform data of a living body related to each person to be examined are stored in advance, the electrocardiogram waveform data serving as reference waveform data, on the basis of produced waveform data served by the produced electrocardiogram waveform data, to specify the reference waveform data of the living body from which the heartbeat signal has been acquired;

a performing process of performing cross-correlation processing between the produced waveform data of which lower-frequency components have been removed and the specified reference waveform data; and a calculating process of calculating an extremal value every period of time from data subjected to $R_{xy}$ in the cross-correlation processing and the heart rate based on the extremal value calculated every period of times, wherein the cross-correlation processing unit calculates $R_{xy}$ defined by the equation (1) every time the delay time τ is shifted by a predetermined amount:

$$R_{xy}(t) = \lim_{T \to 0} \frac{1}{T} \int_{\frac{T}{2}}^{\frac{T}{2}} x(t)y(t+\tau)dt, \tag{1}$$

where x denotes the produced electrocardiogram waveform data of which lower-frequency components have been removed, γ denotes the specified reference waveform data template data, τ denotes a delay time and provides a value of the $R_{xy}$ to the calculation unit.

9. The method according to claim 8, wherein the search process comprising:

a calculating process of calculating a similarity between the produced waveform data produced by the production unit and each set of the reference waveform data stored in the database; and a specifying process of specifying, based on the calculated similarity, the reference waveform data of the living body from which the heartbeat signal has been acquired.

10. The method according to claim 8, wherein the electrocardiogram waveform data produced as the produced waveform data by the production process and each set of electrocardiogram waveform data stored as the reference waveform data in the database include identification information distinguishable from the other electrocardiogram waveform data, respectively;

the method further comprises the setting process of setting identification information to the produced waveform data produced by the production process; and the searching process of searching the database in which the reference waveform data is stored so as to relate to identification information inherent to the living body, on the basis of the identification information of the produced waveform data, to specify the reference waveform data of the living body from which the heartbeat signal has been acquired.

11. The method according to claim 10, wherein the identification information includes at least one of a name showing the living body and a characteristic amount in each set of electrocardiogram waveform information;

the setting process sets, as the identification information, at least one of the name of the living body and the characteristic amount in the reference waveform data; and the searching process searches the database on the basis of the identification information of the produced waveform data, to specify the reference waveform data of the living body from which the heartbeat signal has been acquired, the database storing therein the reference waveform data made to relate to at least one of the name of the living body and the characteristic amount in the reference waveform data.

12. An information recording medium in which a program for measuring a heart rate of a living body is recorded in a readable way by a computer included in a system for measuring a heart rate of the living body based on a heartbeat signal acquired from the living body, the measuring a heart rate program making the computer function as:

an acquiring device for acquiring a heartbeat signal generated in a living body;

a producing device for producing electrocardiogram waveform data of the living body based on the acquired heartbeat signal;

a searching device for searching a database in which at least one set of electrocardiogram waveform data of a living body related to each person to be examined are stored in advance, the electrocardiogram waveform data serving as reference waveform data, on the basis of produced waveform data served by the produced electrocardiogram waveform data, to specify the reference waveform data of the living body from which the heartbeat signal has been acquired;

a performing device for performing cross-correlation processing between the produced waveform data of which lower-frequency components have been removed and the specified reference waveform data; and a calculating device for calculating an extremal value every period of time from data subjected to $R_{xy}$ in the cross-correlation processing and the heart rate based on the extremal value calculated every period of time, wherein the cross-correlation processing unit calculates $R_{xy}$ defined by the equation (1) every time the delay time τ is shifted by a predetermined amount:

$$R_{xy}(t) = \lim_{T \to 0} \frac{1}{T} \int_{\frac{T}{2}}^{\frac{T}{2}} x(t)y(t+\tau)dt, \quad (1)$$

where x denotes the produced electrocardiogram waveform data of which lower-frequency components have been removed, γ denotes the specified reference waveform data template data, τ denotes a delay time and provides a value of the $R_{xy}$ to the calculation unit.

13. The information recording medium according to claim 12, wherein when the computer is made to function as the searching device, the program makes the computer function as:

a similarity calculating device for calculating a similarity between the produced waveform data produced by the producing device and each set of the reference waveform data stored in the database; and a waveform data specifying device for specifying, based on the calculated similarity, the reference waveform data of the living body from which the heartbeat signal has been acquired.

14. The information recording medium according to claim 12, wherein the electrocardiogram waveform data produced as the produced waveform data by the producing device and each set of electrocardiogram waveform data stored as the reference waveform data in the database include identification information distinguishable from the other electrocardiogram waveform data, respectively;

wherein the program makes the computer function as a setting device for setting identification information to the produced waveform data produced by the producing device; and wherein the searching device searches the database in which the reference waveform data is stored so as to relate to identification information inherent to the living body, on the basis of the identification information of the produced waveform data, to specify the reference waveform data of the living body from which the heartbeat signal has been acquired.

15. The information recording medium according to claim 14, wherein the identification information includes at least one of a name showing the living body and a characteristic amount in each set of electrocardiogram waveform information;

wherein the program makes the computer function as:

a setting device for setting, as the identification information, at least one of the name of the living body and the characteristic amount in the reference waveform data; and a searching device for searching the database on the basis of the identification information of the produced waveform data, to specify the reference waveform data of the living body from which the heartbeat signal has been acquired, the database storing therein the reference waveform data made to relate to at least one of the name of the living body and the characteristic amount in the reference waveform data.

16. A system for measuring a heart rate, comprising:

a database in which at least one set of electrocardiogram waveform data of a living body related to each person to be examined are stored in advance, the electrocardiogram waveform data serving as reference waveform data;

an acquisition unit for acquiring a heartbeat signal generated in the living body;

a production unit for producing electrocardiogram waveform data of the living body based on the acquired heartbeat signal;

a search unit for searching the database on the basis of produced waveform data served by the produced electrocardiogram waveform data, to specify the reference waveform data of the living body from which the heartbeat signal has been acquired;

a cross-correlation processing unit for performing cross-correlation processing between the produced waveform data of which lower-frequency components have been removed and the specified reference waveform data;

a calculation unit for calculating an extremal value every period of time from data subjected to $R_{xy}$ in the cross-correlation processing and the heart rate based on the extremal value calculated every period of time; and a control unit for calculating a standard deviation of the R-R intervals acquired in a heartbeat signal generated in the living body, and drawing a comparison between the standard deviation and a predetermined threshold, wherein the cross-correlation processing unit calculates $R_{xy}$ defined by the equation (1) every time the delay time τ is shifted by a predetermined amount:

$$R_{xy}(t) = \lim_{T \to 0} \frac{1}{T} \int_{\frac{T}{2}}^{\frac{T}{2}} x(t)y(t+\tau)dt, \quad (1)$$

where x denotes the produced waveform data of which lower-frequency components have been removed, γ denotes the specified reference waveform data, τ denotes a delay time and provides a value of the $R_{xy}$ to the calculation unit, wherein if the calculated standard deviation is less than the threshold, the control unit concludes that there is no noise, thus operating to give the output of the acquired unit to the production unit, and if the calculated standard deviation is above the threshold, the control unit issues an alarm or re-acquires another heartbeat signal.

17. A system for measuring a heart rate, comprising:

a database in which at least one set of electrocardiogram waveform data of a living body related to each person to be examined are stored in advance, the electrocardiogram waveform data serving as reference waveform data;

an acquisition unit for acquiring a heartbeat signal generated in the living body;

a production unit for producing electrocardiogram waveform data of the living body based on the acquired heartbeat signal;

a search unit for searching the database on the basis of produced waveform data served by the produced electrocardiogram waveform data, to specify the reference waveform data of the living body from which the heartbeat signal has been acquired;

a cross-correlation processing unit for performing cross-correlation processing between the produced waveform data and the specified reference waveform data; and a calculation unit for calculating an extremal value every period of time from data subjected to the cross-correlation processing and the heart rate based on the extremal value calculated every period of time, wherein the cross-correlation processing unit calculates $R_{xy}$ defined by the equation (1) every time the delay time $\tau$ is shifted by a predetermined amount:

$$R_{xy}(t) = \lim_{T \to 0} \frac{1}{T} \int_{\frac{T}{2}}^{\frac{T}{2}} x(t)y(t+\tau)dt, \quad (1)$$

where x denotes the electrocardiogram waveform data of which lower-frequency components have been removed, $\gamma$ denotes the template data, $\tau$ denotes a delay time and provides a value of the $R_{xy}$ to the calculation unit.

* * * * *